US 6,725,720 B2

(12) United States Patent
Kiuchi et al.

(10) Patent No.: US 6,725,720 B2
(45) Date of Patent: Apr. 27, 2004

(54) ROLLING BEARING, AND METHOD OF ULTRASONICALLY DETECTING FLAWS IN BEARING RACEWAY RING OF ROLLING BEARING

(75) Inventors: Akihiro Kiuchi, Kanagawa (JP); Yoichi Matsumoto, Kanagawa (JP); Yasuo Murakami, Kanagawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 10/024,708

(22) Filed: Dec. 21, 2001

(65) Prior Publication Data
US 2002/0121141 A1 Sep. 5, 2002

(30) Foreign Application Priority Data

Dec. 25, 2000 (JP) ................................. P. 2000-391879
Feb. 14, 2001 (JP) ................................. P. 2001-037580
Oct. 19, 2001 (JP) ................................. P. 2001-322280

(51) Int. Cl.$^7$ .......................... G01N 29/04; F16C 33/36; C23C 8/22
(52) U.S. Cl. .......................... 73/593; 384/448; 384/492; 148/906
(58) Field of Search .......................... 73/593, 660, 584, 73/629; 384/448, 492; 148/906

(56) References Cited

U.S. PATENT DOCUMENTS

| 4,307,614 A | * | 12/1981 | Tittmann et al. ............... 73/629 |
| 4,916,751 A | * | 4/1990 | Sumita et al. ............... 384/516 |
| 5,005,417 A | * | 4/1991 | Kawasaki et al. ............ 73/593 |
| 5,890,815 A | * | 4/1999 | Ijuin et al. ................... 384/568 |
| 6,261,004 B1 | * | 7/2001 | Tsujimoto et al. ........... 384/571 |
| 6,342,109 B1 | * | 1/2002 | Takemura et al. ............ 148/319 |
| 6,565,677 B1 | * | 5/2003 | Takemura et al. ............ 148/325 |

FOREIGN PATENT DOCUMENTS

| JP | 3-56640 | 3/1991 |
| JP | 5-117804 | 5/1993 |
| JP | 6-145883 | 5/1994 |
| JP | 6-192790 | 7/1994 |
| JP | 6-307457 | 11/1994 |
| JP | 9-257761 | 10/1997 |
| JP | 11-337530 | 12/1999 |
| JP | 2000-130447 A | 5/2000 |

OTHER PUBLICATIONS

Special Steel vol. 46, No. 6, p. 31, 1997.
Journal of Japanese Society of Tripologists vol. 45, No. 7 (2000) p. 27.
The Society of Materials, Japan, Fatigue Department, The 25$^{th}$ Fatigue Symposium Collection, p. 29.
The Society of Materials, Japan Fracture Mechanics Department, The 14$^{th}$ Tripology Sub–Committee, p. 55.
Influence of Micro–Imperfection Debris.

* cited by examiner

Primary Examiner—Hezron Williams
Assistant Examiner—Rose M. Miller
(74) Attorney, Agent, or Firm—Sughrue Mion, PLLC

(57) ABSTRACT

A surface to serve as a surface under ultrasonic inspection has a roughness of 0.4 μmRa or less, and wherein all imperfections existing a controlled volume X corresponding to all cross sections of a raceway ring 1 assume a length of 0.2 mm or less as represented by the square root of areas of the imperfections. Accordingly, it is possible to provide a rolling bearing which does not become short-lived and obviates a concern about occurrence of cracking even when used in a harsh environment.

12 Claims, 9 Drawing Sheets

LENGTH AS REPRESENTED BY THE ROOT SQUIRE OF AREA OF MAXIMUM NON-METALLIC INTERVENING MATERIAL (μm)

ROUGHNESS OF SURFACE TO BECOME SURFACE
UNDER ULTRASONIC INSPECTION (Ra)

ROLLING BEARING, AND METHOD OF ULTRASONICALLY DETECTING FLAWS IN BEARING RACEWAY RING OF ROLLING BEARING

BACKGROUND OF THE INVENTION

The present invention relates to a rolling bearing which is incorporated into steelworking facilities (facilities for processing steel into products) or paper machine facilities and which is to be used under harsh conditions such as high contact pressure or high temperatures.

The present invention also relates to a rolling bearing for use in railcars such as the Shinkansen (bullet train), a narrow-gauge line, or a freight train.

The present invention further relates to a rolling bearing which is to be used in, e.g., machine tool facilities, for a long period of time at high speed rotation and is subject to high-cycle rolling contact fatigue.

More particularly, the present invention relates to a rolling bearing which is resistant to cracking or flaking, which would otherwise shorten the life of the bearing, and which is ensured of having a stable and prolonged life.

Moreover, the present invention also relates to an ultrasonic detection and inspection method suitable for use in inspecting imperfections in a bearing raceway ring of the rolling bearing, such as presence of non-metallic intevening material in a position immediately below a bearing raceway surface of the bearing raceway ring.

Presence of non-metallic intevening material in a position immediately below a bearing raceway surface of a bearing raceway ring has hitherto been known to greatly affect the life of a rolling bearing. For this reason, there has conventionally been adopted a method of extending the life of a bearing by limiting the amount of non-metallic intevening material in steel during a phase of producing steel material for bearing. As described in, e.g., Japanese Patent Application Laid-Open (i.e., Japanese Patent Unexamined Publication) Nos. 145883/1994, 56640/1991, 117804/1993, and 192790/1994, there has already been proposed a technique aimed at prolonging the life of a bearing. Taught by the technique is that the bearing life can be prolonged by specifying the number of pieces of oxide-based intervening material (imperfections) consisting primarily of $Al_2O_3$ or the number of pieces of Ti-based intervening material (imperfections) consisting primarily of TiN, each existing in a given area of subject steel.

Since a rolling bearing employed in paper machine facilities is used with an inner ring thereof being subjected to fitting stress, hoop stress is exerted on a bearing inner ring in a high-temperature environment, which raises a problem of cracking originating from large pieces of non-metallic intervening material located in the vicinity of an inner-diameter surface. In order to address the problem, there has been adopted a measure for preventing occurrence of cracking, by means of carburization of a bearing surface to there by impart compressive stress to the surface. As described in, e.g., Japanese Patent Application Laid-Open No. 307457/1994, there has already been disclosed a technique of preventing occurrence of hoop stress cracking in an inner ring having fitting stress exerted thereon, which would otherwise be caused in a high-temperature environment, by means of carbonitriding medium carbon steel for preventing occurrence of cracking.

In the case of a bearing for use in a railcar typified by the Shinkansen, in which the bearing is continuously used over a long period of time at high speed, one can predict that the bearing is subject to high-cycle rolling contact fatigue and that a serious accident will arise if the bearing is exfoliated and short-lived. With a view toward reducing the amount of non-metal intervening material in steel, steel having a limited amount of oxygen has been used as bearing material in such an application, or steel having a reduced amount of intervening material existing in a given area of subject steel has been used as bearing material, as described in connection with the related art.

Ultrasonic flaw detection is employed for detecting flaws in steel used in a bearing. With the objective of detecting flaws, such as macro-streak-flaws or imperfections caused by a hole not having been crimped, a steel manufacturer inspects all steel bars and all cross sections thereof, through ultrasonic flaw detection. As a result of removal of the imperfections that have been found through inspection, large imperfections in steel material used for a bearing have been eliminated. As the flaw detection method, there has already been known a normal beam method (see "Special Steel" Vol. 46, No. 46, pg. 31), wherein flaw detection is effected by causing ultrasonic waves to propagate from an outer circumferential surface of rolled steel to the inside thereof, in water or on a table.

However, flaws that can be detected in the rolled steel by ultrasonic flaw detection measure several millimeters in length. In-some instances, flaking or cracking has originated in actually-used bearings, within a short period of time, from large non-metal intervening material of hundreds of micrometers or from an aggregate into which small simple substances have coagulated. Highly accurate detection of flaws of such sizes has been impossible for two reasons. Namely, one of which is that flaws are detected at high speed through inspection during the steelworking process in order to improve productivity, and the other of which is that a steel product is inspected while remaining in a rolled state and having rough crystal grains therein and a rough surface layer. Accordingly, large noise resultantly arises during the course of detection of flaws.

Presence of large non-metallic intervening material has been well known to exert a great influence upon extending the life of a rolling bearing. If presence of such large non-metallic intervening material can be detected beforehand at the time of manufacture of a bearing, an extension of the life of a manufactured bearing can be expected. A steel product to be used for a bearing is subjected to ultrasonic flaw detection in a billet phase during a steel working process or a rolled-round bar phase. However, a flaw detection frequency is as low as 2 through 7 MHz. Hence, a damping factor of ultrasonic waves traveling through steel is low. In terms of roughness of a billet surface and productivity, the time required to pass a steel product through a flaw detector must be minimized. For these reasons, only imperfections of tens of millimeters in length (and hundreds of microns in width) can be detected.

Progress toward increasing load and contact pressure has recently been made in steelworking facilities, and demand for higher temperatures in the field of paper machinery has recently become stricter. For these reasons, a usage environment of a rolling bearing to be incorporated into the facilities has become harsher.

In relation to a rolling bearing used in steelworking facilities and paper machine facilities, there exists demand for a longer life and elimination of products which suddenly become short-lived or which suffer occurrence of cracking. In a production framework in which lines are inspected and maintained at given time intervals, if a rolling bearing used in the line has become short-lived or susceptible to cracking, the line must be deactivated, thereby inflicting an enormous loss. Therefore, there is a need for a rolling bearing which does not become short-lived at high contact pressure and under heavy fitting stress and which obviates a concern about occurrence of cracking and has a stable, long life.

Even in connection with a bearing for use in a railcar, such as the Shinkansen, which is to be continuously used for a long period of time at high speed, a user environment of a bearing has recently become more harsh. In association with an increase in the speed of the Shinkansen, a rolling bearing is exposed to fatigue that is higher in cycles than that having arisen in the related art. Journal of Japanese Society of Tripologists Vol. 45, No. 7 (2000), pg. 27, states that a maintenance-free Shinkansen has recently been planned. In view of facilitating business management of a railroad company, and that there is a desire for increasing an interval for inspection and replacement of a bearing from a current level of 0.9 million kilometers to 1.2 million kilometers and for a maintenance-free bearing of 1.2 million kilometers performance. In these applications, there exists a growing demand for an improvement in reliability of a rolling bearing.

A bearing used in such a train is an important safety component. Occurrence of flaking or cracking in the bearing during operation of a train can lead to a serious accident. Hence, there exists demand for a bearing which is ensured of having a long life and obviates a concern about occurrence of a short-lived bearing even when a bearing has been continuously used over a long period of time at high speed and is susceptible to high-cycle fatigue.

As mentioned previously, with a view toward prolonging life of a bearing in a good lubrication environment, several method have been adopted. That is, a method of limiting the amount of oxygen contained in steel for diminishing non-metallic intervening material, or a method of limiting the amount or size of intervening material present in a given area of object for inspection has been adopted, to thereby extend the life of a bearing. The life of a bearing, as a whole, has been extended, but occurrence of a short-lived bearing has been observed in most cases.

The reason for this is that the related art has not guaranteed absence of intervening material in a raceway ring itself but has limited a typical value of steel to be used. Macro-streak-flaws that suddenly arise within the range of variations in steel have not been specified. When such macro-streak-flaws are present in vicinity of a raceway surface, an unplanned short-lived product is considered to have arisen.

By virtue of considerable study that has been conducted by the present inventors on the rolling bearing set forth, the inventors have found that a short life is ascribable to non-metallic intervening material (imperfections) of tens to hundreds of micrometers located in positions immediately below the bearing raceway surface. Japanese Patent Application Laid-Open No. 130447/2000 has proposed that the fatigue life of the roller is extended by limiting, to 500 $\mu$m or less, the length of non-metallic intervening material existing at depths up to a depth of 2% Da [Da denotes a diameter of a rolling element (in the case of a tapered roller, a mean value obtained by division, by 2, of a sum of a smaller diameter and a larger diameter)], thereby extending rolling fatigue life and obviating a concern about occurrence of a short-lived bearing.

The technique disclosed in Japanese Patent Application Laid-Open No. 130447/2000 is found to prevent shortening of the life of a bearing. As found in the course of considerable studies undertaken by the present inventors, it turns out that, if imperfections, such as large non-metallic intervening material, are present in a position deeper than the bounds specified by the above-described patent, cracking may originate from the imperfections in a case where a bearing is used in a paper machine with, e.g., an inner ring, being subjected to fitting stress.

Continued study by the present inventors reveals that, even in a situation in which a bearing is used under less severe load conditions, the bearing maybe short-lived and susceptible to flaking even in the case of presence of intervening material having a length of 500 $\mu$m or less, if the bearing is used under high-cycle repeated stress. Simultaneously, the inventors have found that limitation of width and length of non-metallic intervening material located within a depth of 2% Da (Da denotes roller diameter) below a bearing raceway surface prolongs the life of a bearing, thus leading to attainment of the present invention.

As a method aimed at inspecting the distribution of comparatively-small non-metallic intervening material in steel, Japanese Patent Application Laid-Open No. 257761/1997 describes a method of detecting small non-metallic intervening material of around 10 micrometers by utilization of high frequency during a billet phase. The method is to regulate the roughness of a sample steel product by means of grinding the surface of the sample, and to inspect an area on the order of, at most, hundreds of square millimeters. Practical inspection of all steel products is difficult.

In a rolling bearing, a raceway surface is repeatedly subjected to rolling fatigue. As has been well known, presence of large non-metallic intervening material in a bearing (particularly in the vicinity of a raceway surface) exerts a great influence on the life of the bearing. For this reason, in order to extend the life of a bearing, there exists a demand for a method of enabling detection of large non-metallic intervening material in all bearing products beforehand. As a method of solving the problem, the present inventors have proposed, as described in Japanese Patent Application Laid-Open No. 337539/1999, a method of detecting large intervening material in all bearing products by means of inspecting a raceway surface of each bearing ring through ultrasonic flaw detection.

More specifically, the invention has been conceived for the purpose of detecting interior large intervening material from a bearing raceway surface and providing a stable and long-life bearing by means of, in combination, detecting flaws to at least a depth of 2 mm below the surface deeper than a position of maximum shearing stress for a bearing by means of an angle beam method, and detecting flaws in bounds deeper than the range covered by the angle beam method by means of the normal beam method.

The present inventors have conducted considerable study on the form of presence of large intervening material in steel detected by the flaw detection method and detection intensity. The inventors have found that some large pieces of intervening material deteriorate detection sensitivity under the conventional method.

SUMMARY OF THE INVENTION

As mentioned previously, the method of detecting non-metallic intervening material has been put forward as described in Japanese Patent Application Laid-Open NO. 337530/1999. As a result of considerable study on an improvement in the sensitivity of detection of intervening material whose size is limited by the invention, the inventors have found that imperfections of tens of micrometers can be detected accurately within all cross sections of a bearing by limiting surface roughness of a bearing raceway surface (for increasing a signal-to-noise ratio of an ultrasonic echo).

The present invention has been conceived on the basis of the drawbacks and findings described above. The present invention aims at providing a rolling bearing, a bearing, and a bearing raceway ring ultrasonic flaw detection method. More specifically, there is provided a rolling bearing that does not become short-lived and obviates a concern about occurrence of cracking even when used in a harsh/severe environment, such as under heavy load and high contact pressure as in the case of a bearing for use in steelworking or at high temperatures with an inner ring thereof being subjected to fitting stress as in the case of a paper machine bearing. There is also provided a bearing which is to be used in an environment, in which the bearing is subjected to high-cycle rolling fatigue stemming from high-speed rotation, as in the case of a bearing used for a railcar such as the Shinkansen or in a machine tool, and which is assured of having no large flaws typified by non-metallic intervening material in the entire volume of a bearing in the vicinity of a raceway surface and a long life without involving a concern about occurrence of a short-lived bearing or a cracked bearing. There is further provided a bearing raceway ring ultrasonic flaw detection method for use with the rolling bearing and with the bearing set forth.

To solve the problems, the present invention provides a rolling bearing, wherein a bearing raceway ring of at least one of inner and outer rings has a surface (such as a raceway surface) which has a roughness of 0.4 μmRa or less and is to act as a surface under ultrasonic inspection, and wherein an imperfection existing in a controlled volume including the axis of rotation of the raceway ring and all cross sections parallel to the rotation axis of the raceway ring assumes a length of 0.2 mm or less as represented by the square root of area of the imperfection.

Here, the term "controlled volume" designates a volume obtained by means of rotating a hatched cross section X shown in FIG. 1 in the direction of circumference of the raceway ring. In the following description, the cross section will be sometimes called all cross sections located below a raceway surface.

The surface under ultrasonic inspection is a raceway surface, normally.

Imperfections or flaws refer to non-metallic intervening material or an aggregate consisting of pieces of non-metallic intervening material.

A steel bearing typified by a roll-neck bearing is used under heavy load and at high contact pressure. Progress has recently been made on miniaturization of rolling mill facilities, and advancement is also made on miniaturization of a housing having a bearing inserted therein. For example, if a housing becomes deficient in rigidity, there may arise a case where an outer ring is subjected to repeated bending stress as a result of the bearing following the housing.

An inner ring of a paper machine bearing is used while subjected to fitting stress. In a recent ever-increasing high-temperature environment, large hoop stress is exerted on the inner ring of the bearing. There arises a case where cracking originates in large non-metallic intervening material located in the vicinity of an inner-diameter surface.

A result of study on this problem conducted by the present inventors shows that, even in the case of imperfections (including an aggregate of non-metallic intervening material pieces, and the same applies to other, corresponding cases) existing in a controlled volume of all cross sections located below a raceway surface having a length of 0.5 mm or more, if the imperfections assume a length of 0.2 mm or less as represented by the square root of areas of the imperfections, there are prevented shortening of life of the bearing and occurrence of cracking, which would otherwise originate from the imperfections.

Here, the "length as represented by the root square of area of an imperfection" means a value represented by the "square root of a product of length and width of an imperfection within a plane located in a position where the imperfection is of maximum size." Attention has been drawn to the largest piece of intervening material existing in all cross sections. Origination of cracking is found to be attributable to a combination of the length of an imperfection and a given width or more thereof. For this reason, the size of an imperfection is specified as a length as represented by the root square of area of the imperfection. The present invention specifies the maximum length represented by the root square of area of the imperfection as being a value of 0.2 mm or less.

If hoop stress is exerted on a bearing; e.g., an inner ring, maximum tensile stress develops in a raceway surface. Here, the tensile stress diminishes further toward the inside thereof (i.e., in the direction of outside diameter). If large intervening material is present at any point along the direction of tensile stress, the stress concentrating at the intervening material becomes greater, thereby resulting in occurrence of cracking.

In this regard, the result of the study conducted by the present inventors shows that, when all cross sections located below a surface of a raceway ring under ultrasonic inspection are taken as a controlled volume, there can be prevented occurrence of cracking, which would otherwise originate from imperfections across all the cross sections of the bearing including surroundings of a surface, by means of setting the size of an imperfection (including an aggregate of non-metallic intervening material pieces) to a length of 0.2 mm or less as represented by the square root of area of the imperfection.

As mentioned above, in relation to a bearing to be used in a harsh environment, such as under high pressure and high temperature, the size of an imperfection existing in the controlled volume including an axis of rotation of the raceway ring and all cross sections parallel to the rotation axis is set to a length of 0.2 mm or less as represented by the square root of area of the imperfection.

Imperfections described in connection with the present invention refer to imperfections (including intervening material, macro-streak-flow, void, crack, and so on) of various shapes, such as linear imperfections, oval imperfections, or spherical imperfections. An imperfection echo serving as an imperfection signal is emitted to the area of an imperfection. The area of an imperfection echo is transformed into the area of an imperfection, and the size of the imperfection is defined as a length as represented by the root square of area of the imperfection.

Note that in the specification, when the area of the imperfection is a linear or rectangular shape, the length represented by the root square of area of the imperfection is directed to a length represent by a root square of area defined by multiplying a longitudinal length by a lateral length. Further, in the specification, when the area of the imperfection is an ellipse or circle shape, the length represented by the root square of area of the imperfection is directed to a length represent by a root square of area defined by multiplying the longest diameter by the shortest diameter.

Japanese Patent Application Laid-Open No. 337530/1999 describes a method of detecting non-metallic intervening material of tens to hundreds of micrometers by taking, as a controlled volume, a cross section including a deep location below a raceway surface of a raceway ring. A result of further continued study on enhancement of detection accuracy of ultrasonic flaw detection shows that an imperfection of tens of micrometers over all cross sections of the bearing can be detected accurately by means of limiting surface roughness of the bearing raceway surface.

More specifically, this flaw detection method was proposed as described in Japanese Patent Application Laid-Open No. 337530/1999. In this patent, a bearing which has been ground after heating is taken as favorable. However, a further study on the method shows presence of a range of surface roughness suitable for detection.

A result of a survey on the relationship between surface roughness and detection intensity shows that an ultrasonic flaw detection signal assumes a superior signal-to-noise ratio with regard to intensity at a surface roughness of 0.4 μmRa or less. Detection intensity is found to be deteriorated at surface roughness greater than this, thereby posing difficulty in detecting imperfections of the sizes specified by the invention.

For these reasons, the roughness of a surface under ultrasonic inspection (usually a raceway surface) to be subjected to ultrasonic flaw detection is specified as being a value of 0.4 μmRa or less.

According to the invention, there is also provided a rolling bearing, wherein a raceway ring of at least one of inner and outer rings has a surface (such as a raceway surface) which has a roughness of 0.4 μmRa or less and is to act as a surface under ultrasonic inspection, and wherein an imperfection existing in a controlled volume which is a product of (a 2% Da depth of the surface under ultrasonic inspection) and (the surface under ultrasonic inspection) assumes a length of 0.2 mm or less as represented by the square root of area of the imperfection and/or is smaller than $\sqrt{(area)}_{MAX}$ or less.

$$\sqrt{(area)}_{MAX} = [(1.56 \cdot Hv + 187) \times (0.77/(\tau_{st})_{MAX})]^6 \quad (1)$$

where $(\tau_{st})_{MAX}$ is the maximum shearing stress induced by rolling load on the surface (such as the raceway surface), and Hv is Vickers hardness in the position of the maximum shearing stress beneath the surface.

A length as represented by the root square of area of an imperfection means the root square of an imperfection area.

Further, the term "2% Da depth" means a 2% Da depth immediately below a bearing raceway surface. Da means a diameter of a rolling element (in the case of a tapered roller, a mean value obtained by division, by 2, of a sum of a smaller diameter and a larger diameter).

A surface under ultrasonic inspection usually means a raceway surface.

A position of maximum shearing stress is a 2% Da depth from the raceway surface.

The area defined by "a product of (a 2% Da depth of the surface under ultrasonic inspection) and (the surface under ultrasonic inspection)" corresponds to, e.g., an area designated by Y shown in FIG. 2.

In connection with a bearing for use in the Shinkansen, as a result of a recent increase in the speed of the Shinkansen (bullet train), the operation speed of some trains has reached a maximum of 300 km/hr. An increase in the operation speed of trains involves further weight reduction of railcars. With regard to bearings, there have hitherto been employed a cylindrical rolling bearing subjected to radial load and a ball bearing subjected to irregular thrust load. In contrast, a conical rolling bearing capable of being simultaneously subjected to radial load and thrust load has recently been employed [see Journal of Japanese Society of Tripologists Vol. 45, No. 7 (2000), pg. 27].

For these reasons, working conditions for a bearing are considered to have become more harsh than those for conventional bearings.

A result of the study conducted by the present inventors shows that a bearing will be subjected to flaking and become short-lived in an environment in which the bearing is susceptible to high-cycle rolling fatigue at high speed, when non-metallic intervening material existing in a controlled volume which is a product of (a 2% Da depth of the surface under ultrasonic inspection) and (a raceway surface); that is, a controlled volume which is a product of (a 2% Da depth of the surface under ultrasonic inspection) and (the surface under ultrasonic inspection), becomes greater than a given value. Determination of a critical size of intervening material has lead to the present invention.

When working conditions have reached a certain level or higher; that is, when intervening material is smaller than a length of 0.2 mm or less as represented by the square root of area of the intervening material, the critical value differs according to the working conditions. Exfoliation is found to arise under conditions in which the size of intervening material exceeds a critical value $\sqrt{(area)}_{MAX} (= [(1.56 \cdot Hv + 187) \times (0.77/(\tau_{st})_{MAX})]^6$, where $(\tau_{st})_{MAX}$ is the maximum shearing stress imposed on a bearing and a rolling element.

In other words, under less harsh working conditions, no flaking arises if the size of intervening material is smaller than a length of 0.2 mm or less as represented by the square root of area of the intervening material. The invention according to second aspect of the present invention has been conceived on the basis of this finding.

If working conditions become harsher, flaking will arise even in the case of a length of 0.2 mm or less in terms of square root of area of an imperfection. As mentioned above, the critical value is expressed by $\sqrt{(area)}_{MAX} = [(1.56 \cdot Hv + 187) \times (0.77/(\tau_{st})_{MAX})]^6$. An invention according to third aspect of the present invention has been conceived on the basis of the critical value.

An idea presumed from the expression is described as follows.

A quantitative relationship between the size of intervening material and rolling fatigue strength has not yet been obtained. There have already been obtained a bearing steel strength of $\Delta K_{1th} = 5.8$ MPa$\sqrt{(m)}$ [The Society of Materials, Japan, Fatigue Department, The 25$^{th}$ Fatigue Symposium Collection, Yoshio FUJII et al., pg. 29, (2000)]; and a bearing steel strength of $\Delta K_{2th} = 14$ MPa$\sqrt{(m)}$ [The Society of Materials, Japan, Fracture Mechanics Department, The 14$^{th}$ Tripology Sub-Committee, Yoshinobu MURAKAMI et al., pg. 55, (2000)]. Provided that $\Delta K_{1th} < \Delta K_{2th}$, when flaking originates in non-metallic intervening material, fatigue cracks are considered to originate from non-metallic intervening material in $K_1$ mode. In connection with $K_1$ mode, as described in "Influence of Micro-Imperfection Debris" (Yoshinobu MURAKAMI, Yokendo (Corporation), Mar. 8, 1993), Eq. (2) provided below is deduced from many data sets as an equation for determining a fatigue limit of $10^7$ cycles for internally-originated imperfections.

$$\sigma w = 1.56(Hv+120)/\{\sqrt{(area)}^{1/6}\} \quad (2)$$

Here, $\sqrt{(area)}$ means a length as represented by the root square of area of an imperfection, and Hv means the hardness of a point of origin.

Here, $\Delta K_{1th}$ and $\Delta K_{2th}$ each represent a threshold stress intensity factor and mean that, if fatigue cracks have become greater in $K_1$ and $K_2$ modes, the cracks will enter a stable growth phase. Here, the unit is MPa√m.

Here, √m means the half power of meter (=$m^{1/2}$)

Here, $K_1$ mode means a coefficient showing the strength of stress field in the vicinity of the extremity of a crack, and cracks in $K_1$ mode exhibit a style of pulled deformation.

$K_1$ is known as a critical stress expansion coefficient for cracks of open type, and $K_2$ mode is known as a critical stress expansion coefficient for cracks of sheared type.

The above concept is based on the finding that a fatigue limit of material is dependent on the size of intervening material from which cracks originate and the hardness of the intervening material. A result of the life test conducted by the present inventors under various conditions (according to the size of intervening material pieces found through ultrasonic flaw detection and variations in test load) on the basis of Eq. (2) shows that, in connection with flaking of a bearing, there exists a correlation between the size of intervening material and the maximum shearing stress developing between a rolling element and inner and outer rings at the time of use.

If intervening material of $\sqrt{(area)}_{MAX}$ is present under the conditions for Eq. (1), flaking will arise. This has been found in applicable to a case where intervening material measures 0.2 mm or more and flaking will be induced by even small shearing stress.

As mentioned above, the method of detecting the imperfections has been proposed as described in Japanese Patent Application Laid-Open No. 337530/1999. In this case, a bearing which has been ground after having been thermally treated is considered preferable. However, the continued research conducted thereafter shows that there are bounds for surface roughness suitable for detection. A result of a survey on the relationship between surface roughness and detection intensity shows that an ultrasonic flaw detection signal assumes a superior signal-to-noise ratio with regard to intensity at a surface roughness of 0.4 $\mu$mRa or less. Detection intensity is found to deteriorate at surface roughness greater than this, thereby posing difficulty in detecting imperfections of the sizes specified by the invention. For these reasons, surface roughness is specified as being the above-described value.

A bearing raceway ring ultrasonic imperfection (such as flaw) detection method, in which ultrasonic waves are emitted from a probe to a surface to serve as a surface under ultrasonic inspection of a bearing raceway ring, and imperfections are detected by means of reflection of an echo, wherein flaws or imperfections are detected to a depth of 2 mm below at least a position of the maximum shearing stress on the bearing raceway ring by means of at least one of the surface beam detection method and ultrasonic flaw detection method.

In the above-mentioned method, a flat beam probe of non-focus type may be used for at least one method.

In the above-mentioned method, it is preferable to further comprises the step of detecting a bearing raceway ring as a non-defecting one if all of imperfection of the bearing has a lenth of 0.2 mm or less as represented by the square root of area of the imperfection.

An invention described in fifth aspect of the present invention provides a rolling bearing, wherein a raceway ring of at least one of inner and outer rings has a surface which has a roughness of 0.4 $\mu$mRa or less and is to act as a surface under ultrasonic inspection, and wherein each of the imperfections detected by the ultrasonic flaw detection method described in fourth aspect of the present invention assumes a length of 0.2 mm or less as represented by the square root of area of the imperfection.

According to the invention described in fifth aspect of the present invention, flaw detection methods matching the shape of large intervening material which is an object of inspection are selected or used in combination. As a result, detection of intervening material of any shape or form is possible. According to the invention defined in fifth aspect of the present invention, there can be provided a rolling bearing using a raceway ring, in which the size of contained intervening material is suppressed to a desired size without fail by means of the detection method.

As mentioned previously, as described in Japanese Patent Application Laid-Open No. 337530/1999, the present inventors have proposed a bearing ring ultrasonic flaw detection method for ensuring a stable, long-life bearing by means of detecting and removing large intervening material located immediately below a rolling bearing raceway surface through ultrasonic flaw detection of all bearings. However, a result of continued study shows that intervening material of, e.g., several millimeters in length having a small width, sometimes fails to be detected by the angle beam method using a conventional probe of point focus type. Use of a probe of 2 to 15 MHz flat beam type (non-focus type) is found to enable detection of the intervening material of such shape and form with a superior signal-to-noise ratio. Thus has been conceived the present invention.

The reason why the probe of point focus type fails to detect intervening material is considered to be as follows. A probe of point focus type concentrates ultrasonic energy at a focal point, thus exhibiting a great detection ability. However, the diameter of the focal point measures hundreds of microns or thereabouts. At the time of flaw detection operation, the focal point of energy moves in the vertical and horizontal directions at pitches smaller than the diameter of the focal point, thus detecting flaws or imperfections within a target area. Consequently, detection of a large imperfection is determined by means of detecting flaws or imperfections on a focal-point-by-focal-point basis and linking together the thus-detected points to determine the overall size and length of the imperfection. For example, if there is large intervening material having a width of 50 microns and a length of 5 mm, a probe of point focus type detects the maximum intervening material piece as having a width of 50 microns and a length corresponding to the width of the beam spot (about 0.5 mm). Consequently, the intensity of imperfection echo at each focal point is considered not to become greater.

In contrast, a probe of flat beam type has a minimum of beam diameter of 5 mm or more. In the case of an imperfection which is an object of detection in the present invention, the entirety of the imperfection falls within the diameter of a single beam spot. A resultant echo has comparatively high intensity, and detection of the imperfection is feasible.

The probe of flat beam type is found to have a higher capability to detect elongated intervening material than does the probe of point focus type. The problem can be solved by use of the probe of flat beam type in conjunction with a surface flaw detection method; that is, at least one of the angle beam method and the surface wave flaw detection method. Thus has been conceived the present invention.

As described in Japanese Patent Application Laid-Open No. 337530/1999, a flaw detection frequency ranging from 2 MHz through 30 MHz has been put forward. In general, as a frequency becomes higher, the minimum detectable size of an imperfection becomes smaller. Hence, a higher frequency is beneficial for detecting large intervening material. In a case where the surface wave flaw detection method is employed, a signal-to-noise ratio of an imperfection is admitted to have a tendency of becoming deteriorated with an increase in frequency. From this, a range of 2 MHz to 10 MHz is found to be suitable. In relation to the invention defined in fourth aspect of the present invention, the flaw detection frequency is preferably set to a range of 2 MHz to 10 MHz, in view of enhancement of detection sensitivity.

Moreover, the above-mentioned object can also be achieved by a bearing raceway ring ultrasonic imperfection detection method for a rolling bearing that comprises a bearing raceway ring having a raceway surface which has a roughness of 0.4 μmRa or less, the method comprising:

detecting a bearing raceway ring as a non-defecting one if all of imperfection of the bearing raceway ring has a length of 0.2 mm or less as represented by the square root of area of the imperfection.

BRIEF DESCRIPTIONS OF DRAWINGS

FIG. 5 shows heating conditions, wherein

DETAILED DESCRIPTION OF THE PREFERRED EMBODIMENTS

A first embodiment of the present invention will now be described.

Figure 1:
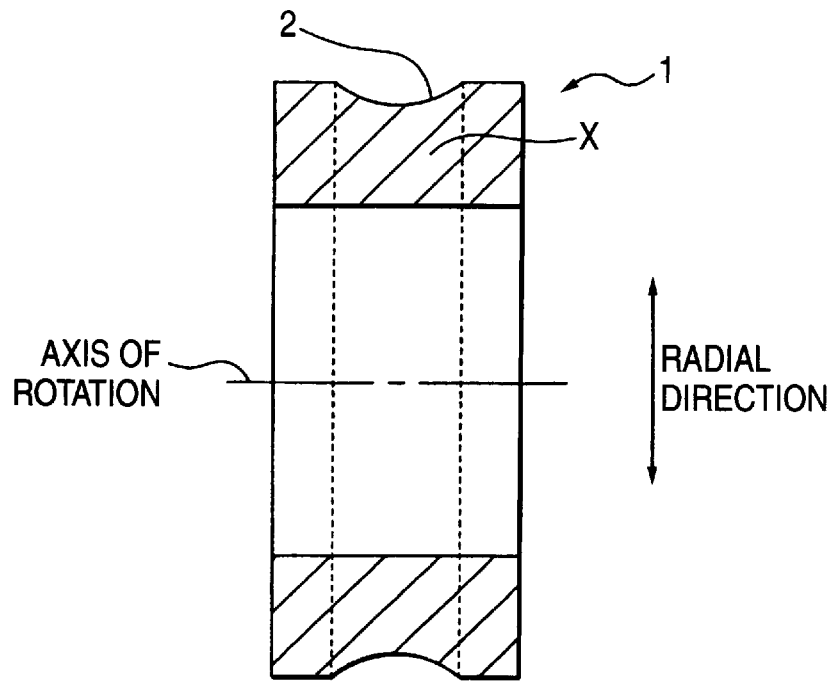
FIG. 1 is a cross-sectional view showing a controlled volume of an inner ring according to a first embodiment of the present invention.

FIG. 1 illustrates an inner ring serving as a bearing raceway ring. However, an outer ring may also be employed. Alternatively, both inner and outer rings may be caused to satisfy the requirements described previously.

A raceway surface 2 of the raceway ring 1 is finished to a surface roughness of 0.4 μmRa or less by means of polishing.

All cross sections of the raceway ring 1 are subjected to ultrasonic flaw detection. There is eliminated a raceway ring 1 including non-metallic intervening material (imperfections) larger than a length of 0.2 mm as represented by the square root of area of the imperfection.

More specifically, a rolling bearing, such as a cylindrical rolling bearing, is constituted through use of the raceway ring 1 including imperfections which exist in the controlled volume including all cross sections of the raceway ring 1 and which have a length of 0.2 mm or less as represented by the square root of area of the imperfection.

In relation to the rolling bearing having the foregoing construction, all bearings can be inspected with regard to a controlled volume containing all cross sections of the raceway ring 1; that is, all cross sections of a bearing, by means of specifying the roughness of a surface under ultrasonic inspection to be exposed to ultrasonic waves (primarily the raceway surface 2) to a value of 0.4 μmRa or less. As a result, there can be detected without fail imperfections which are longer than a length of 0.2 mm as represented by the square root of area of the imperfection.

All the imperfections existing in all cross sections assume a length of 0.2 mm or more as represented by the square root of areas of the imperfections. Even when the rolling bearing is used as a steel bearing to be used under heavy load and at high pressure, typified by a roll neck bearing, the bearing will become not short-lived but long-lived and stable without involving a concern about occurrence of cracking. As a result, there is prevented occurrence of unplanned stoppage of a steelworking line because of a rolling bearing failure.

Although the inner ring of a paper machine bearing is used while being imparted with fitting stress, greater hoop stress is exerted additionally on the inner ring in a recent ever-increasing high-temperature environment. Even in the case of an imperfection (including an aggregate of non-metallic intervening material pieces) existing in a controlled volume of all cross sections of a bearing ring having a length of 0.5 mm or more, if each imperfection assumes a length of 0.2 mm or less as represented by the square root of area of the imperfection, there are prevented shortening of life of the bearing and occurrence of cracking, which would otherwise originate from the imperfections.

A second embodiment of the present invention will now be described by reference to the accompanying drawings.

Figure 2:
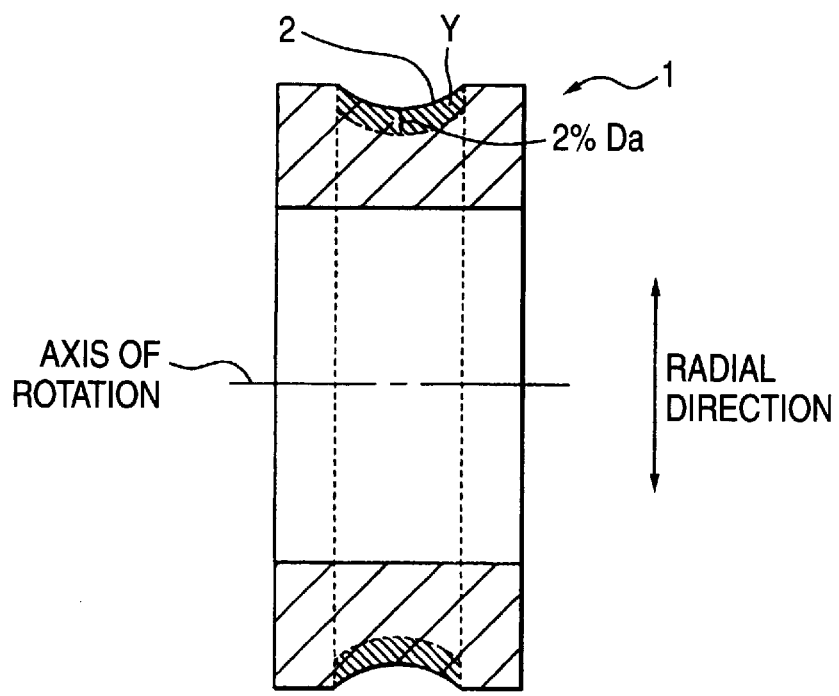
FIG. 2 is a cross-sectional view showing a controlled volume of an inner ring according to a second embodiment of the present invention.

FIG. 2 illustrates an inner ring serving as a bearing raceway ring. However, an outer ring may also be employed. Alternatively, both inner and outer rings may be caused to satisfy the requirements described previously.

A raceway surface 2 of the raceway ring 1 is finished to a surface roughness of 0.4 μmRa or less by means of polishing.

All cross sections of the raceway ring 1 located below the raceway surface 2 are subjected to ultrasonic flaw detection. There is eliminated a raceway ring 1 including an imperfection which exists in a controlled volume corresponding to a product of (a 2% Da depth of the surface under ultrasonic inspection) and (the surface under ultrasonic inspection) and is smaller than a length of 0.2 mm as represented by square root of area of the imperfection or smaller than $\sqrt{(area)}_{MAX}$.

A rolling bearing, such as a cylindrical rolling bearing, is constituted through use of the raceway ring 1 including imperfections which exist in a controlled volume corresponding to a product of (a 2% Da depth of the surface under ultrasonic inspection) and (the surface under ultrasonic inspection), which assume a length of 0.2 mm or less as represented by the square root of area of the imperfection, and which are smaller than $\sqrt{(\text{area})_{MAX}}$.

In relation to the rolling bearing having the foregoing construction, all bearings can be inspected with regard to a controlled volume to a 2% Da depth below the raceway surface 2 through ultrasonic flaw detection, by means of specifying the roughness of a surface under ultrasonic inspection to be exposed to ultrasonic waves (primarily the raceway surface 2) to a value of 0.4 µmRa or less. As a result, there can be detected without fail imperfections which are longer than a length of 0.2 mm as represented by the square root of area of the imperfection or longer than $\sqrt{(\text{area})_{MAX}}$.

Eventually, a bearing is assured of being free of imperfections, as typified by large metallic intervening material in the total volume of a neighborhood of the raceway surface of the bearing, and is assured of involving no concern about occurrence of a short-lived or cracked bearing, even when used under a condition in which the bearing is subjected to high-cycle rolling fatigue due to high-speed rotation, as in the case of a bearing for use in a railcar such as the Shinkansen or a bearing for use in steelworking facilities.

In the present embodiment, both a value of 0.2 mm and the critical value $\sqrt{(\text{area})_{MAX}}$ are employed as upper limits of length as represented by the root square of area of an imperfection; that is, $\sqrt{(\text{area})}$. However, unless working conditions for a bearing are harsh, it is possible to adopt only a value of 0.2 mm.

A third embodiment of the invention will now be described by reference to the accompanying drawings.

Figure 3:
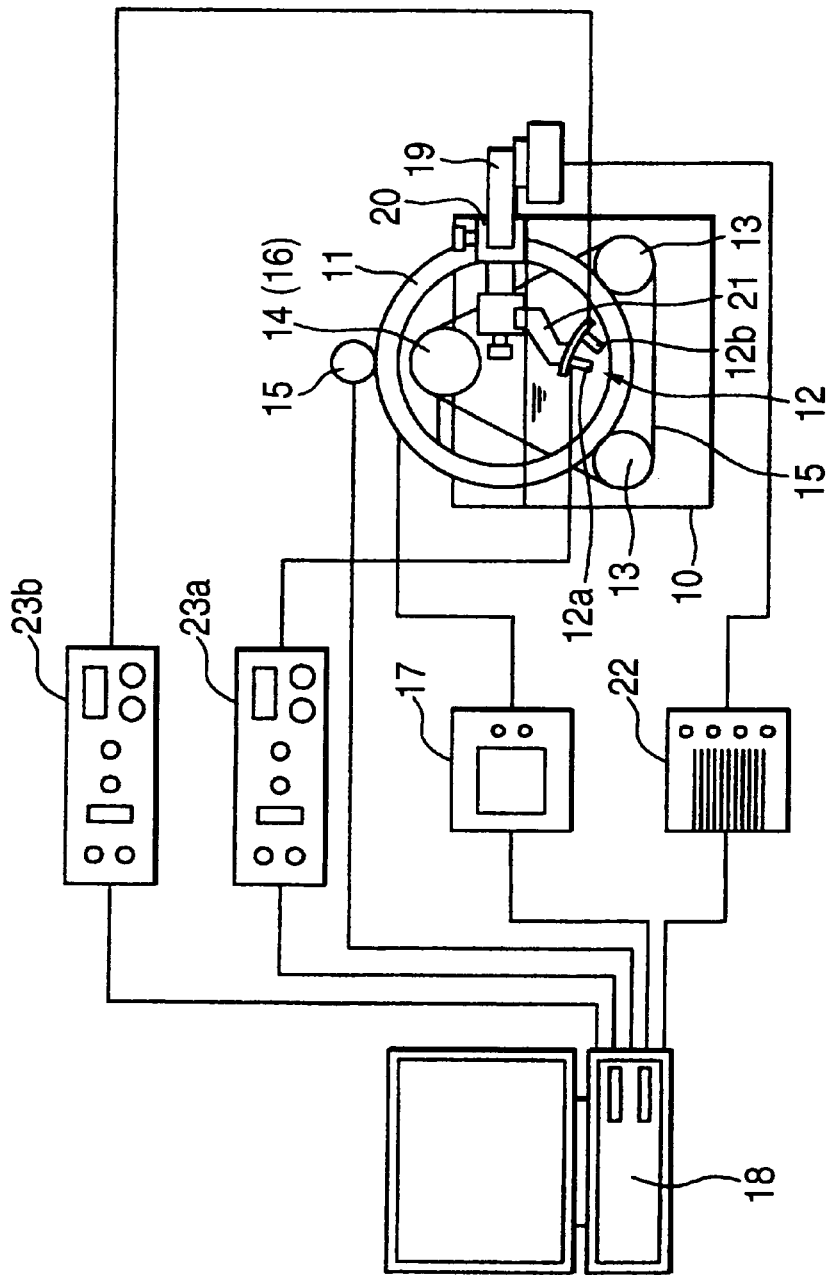
FIG. 3 is an illustration showing an ultrasonic flaw detector according to a third embodiment of the present invention.

FIG. 3 is a schematic diagram showing an ultrasonic flaw detector to be employed in the present embodiment.

Reference numeral 10 provided in FIG. 3 designates a tank in which water serving as an ultrasonic wave transmission medium is stored. A raceway ring 11 of a rolling bearing serving as an object of inspection and an ultrasonic flaw detection probe 12 are immersed in the water of the tank 10. The ultrasonic flaw detection probe 12 has a probe 12a for use with the angle beam method and a probe 12b for use with surface wave flaw detection, the probes being provided separately.

The raceway ring 11 is placed on two pulleys 13 which are located in the tank and horizontally spaced apart from each other. A belt 15 is wrapped in an equilateral triangle around the pulleys 13 and a pulley 14 fixed to a motor shaft of a rotary drive motor 16. The rotary drive motor 16 is controlled by a controller 18 via a motor drive control amplifier 17. The raceway ring 11 placed on the pulleys 13, 14 is rotated at predetermined speed, by means of driving action of the rotary drive motor 16. Here, the controller 18 is constituted of a personal computer or a like device equipped with display means such as a CRT.

The ultrasonic flaw detection probes 12a, 12b are mounted, via a probe mount 21, on an X-Y stage 20 supported by a linear guide device 19 situated so as to be movable along an axial direction of the raceway ring 11. The probes 12a, 12b are disposed so as to oppose the raceway surface 2 of the raceway ring 11. The probes 12a, 12b respectively emit, toward the raceway surface of the raceway ring, ultrasonic pulses corresponding to voltage signals output from respective ultrasonic flaw detectors, and receive echoes reflected from the raceway ring. The thus-received echoes are converted into a voltage signal, and the voltage signal is transmitted to either an ultrasonic flaw detector 23a or an ultrasonic flaw detector 23b.

In accordance with an instruction output from the controller 18, each of the ultrasonic flaw detectors 23a, 23b individually transmits to the corresponding ultrasonic flaw detection probe 12a or 12b an instruction signal consisting of a voltage signal. Further, each of the detectors 23a, 23b sends to the controller 18 flaw detection information prepared on the basis of the transmitted and received signals, and the controller 18 displays the information on the CRT.

The linear guide 19 moves the ultrasonic flaw detection probe 12a or 12b in the axial direction of the raceway ring 11 through use of an unillustrated servo motor controlled by a linear guide controller 22. When a rotary encoder provided on an outer circumferential surface of the raceway ring 11 detects that the raceway ring 11 has made one rotation (through 360°), the linear guide controller 22 controls the servo motor in accordance with an instruction output from the controller 18, thereby moving the ultrasonic flaw detection probe 12a or 12b over a predetermined distance in the axial direction of the raceway ring 11. As a result, all cross sections located below the overall raceway surface of the raceway ring 11 are subjected to flaw detection. In the present embodiment, an outer ring is illustrated as the raceway ring 11. However, if the position of the probe 12 and those of the pulleys 13 are switched, the present embodiment is also applicable to an inner ring.

Flaw detection conditions for the ultrasonic flaw detector are set as follows:

(1) Surface flaw detection method (corresponding to flaw detection operation performed by the devices 12a and 23a)

Incident angle: 28° through 30°

Probe: 5 MHz flat beam type

Transducer diameter: 6 mm

Water distance: 20 mm (2) Angle beam method (corresponding to flaw detection operation performed by the devices 12b, 23b)

Incident angle: 25°, 19°, 14°

Probe: 10 MHz point focus type

Underwater focal distance: 20 mm

Transducer diameter: 6 mm

Water distance: 20 mm

Flaw detector: HIS2 (Krautokramer Japan, Co., Ltd.)

Flaw detection pitch: 0.05 mm pitch/rotation in both circumferential and axial directions Surface flaws having a depth of 0.05 mm, a width of 0.1 mm, and a length of 5 mm are formed in a prism-shaped steel product whose surface has been finished by polishing, by means of electric discharge machining. Flaw detection sensitivity is adjusted such that the height of maximum echo reflected from the flaw assumes a value of 100 when flaw detection operation is performed under the foregoing conditions.

Under the previously-described conditions, the bearing to be inspected and the flaw detection probes are immersed in water. By means of the surface wave flaw detection method and the angle beam method, flaws are detected from the raceway surface which is to act as a surface under ultrasonic inspection, to a depth of 2 mm from the position of maximum shearing stress.

If, for example, at least one of flaw detection results concerning a bearing shows a signal-to-noise ratio of 3 or more, the bearing is acknowledged as a defective bearing. Subsequently, an imperfection echo intensity regarding the bearing obtained according to each of the methods is recorded.

The signal-to-noise ratio is an illustrative example, and hence there may be set a value optimal for the form of a defective which is to be inspected.

According to the present embodiment, imperfections which are deleterious to the life of a bearing and exist immediately below a raceway surface of a bearing raceway ring can be detected efficiently.

Deleterious imperfections come in a variety of types, ranging from narrow, elongated imperfections to round imperfections. Under the method according to the embodiment of the present invention, imperfections of all forms can be detected efficiently.

Particularly, when there is selected a raceway ring including imperfections having a length of 0.2 mm or less as represented by the root square of area of the imperfection, imperfections of any geometry can be detected without fail by adoption of the ultrasonic flaw detection method. Hence, a bearing can be assured of having no deleterious imperfections within bounds ranging from a neighborhood of a raceway surface of a raceway ring to the inside thereof, which are subjected to rolling fatigue stress. In other words, there can be eliminated a concern about occurrence of a short-life bearing, and provision of a rolling bearing assured of having a long life becomes feasible.

The present embodiment has provided an example of use of a probe of flat beam type as the surface wave flaw detection probe. However, a probe of flat beam type may be used as a probe for the angle beam method. Alternatively, probes of flat beam type may be used for both flaw detection methods. According to the form of an imperfection to be detected, a probe of flat beam type and a probe of point focus type may be used appropriately in combination.

EXAMPLES

Examples 1 and 2 provided below relate to the invention defined in first aspect of the present invention; Example 3 relates to the invention defined in second aspect of the present invention; and Example 4 relates to the invention defined in third aspect of the present invention.

Example 1

Figure 4:
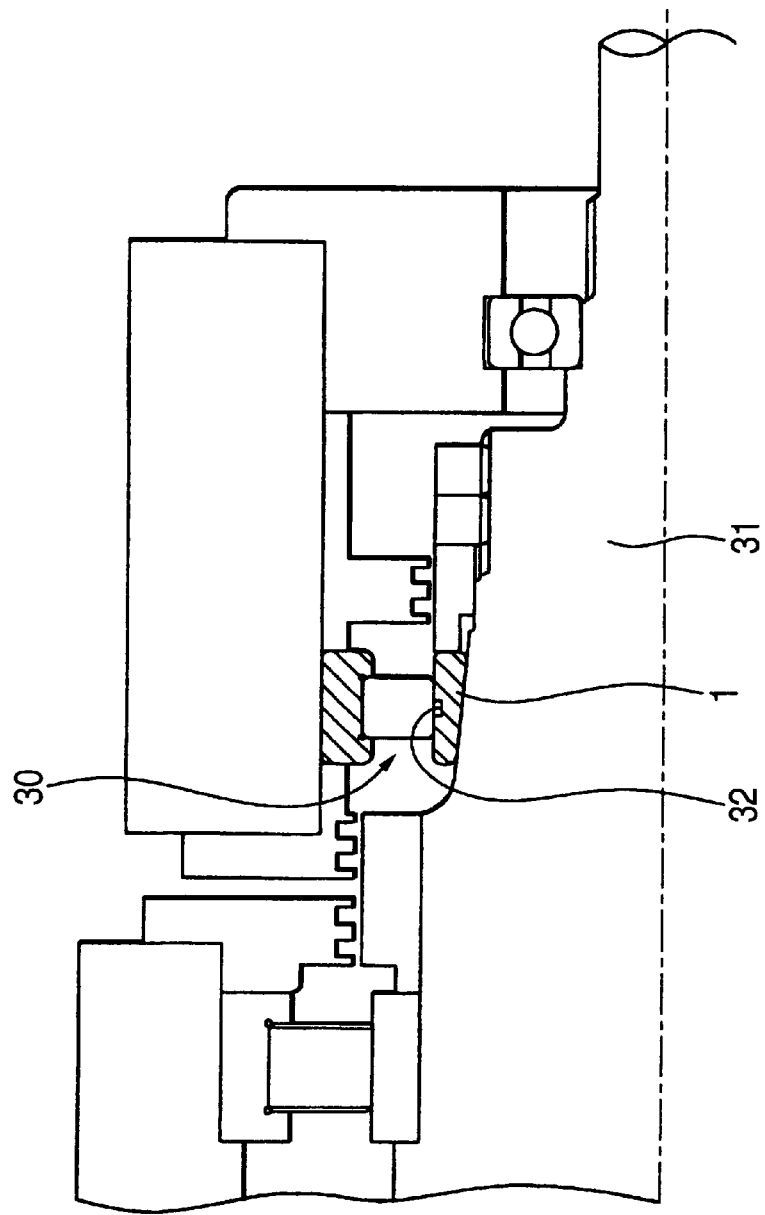
FIG. 4 is an illustration showing an inner ring crack life tester.

Inner rings 1 for bearings were constituted through use of various types of steel materials provided in Table 1, and the thus-constituted inner rings 1 were subjected to a cracking life test through use of test equipment such as that shown in FIG. 4.

Figure 5A:
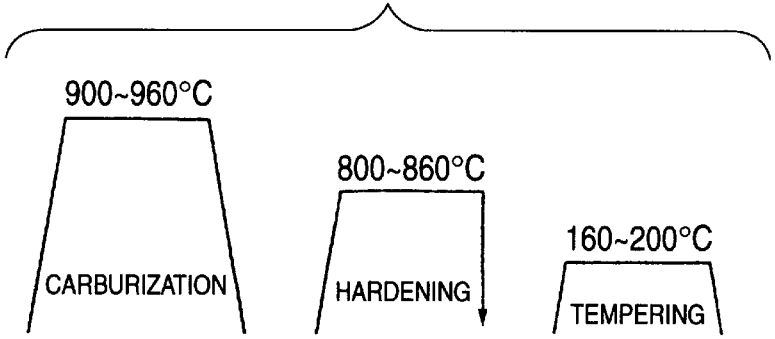
FIG. 5A shows heating conditions for carburized steel and FIG. 5B shows through-hardened steel.
Figure 5B:
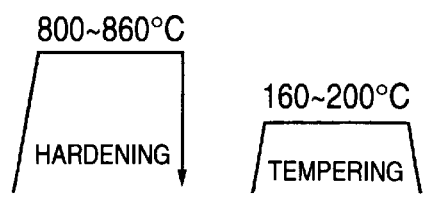

Manufacture of the inner rings 1 was effected by means of: forming steel materials of respective types into inner rings; subjecting the inner rings to heat treatment shown in FIGS. 5A and 5B; and finishing the thus-heated inner rings by means of polishing, whereby the inner rings 1, each having a tapered inner diameter, were produced.

As shown in FIG. 5A, steel materials according to Examples 2, 3, and 5 and those according to Comparative Examples 1 and 3 provided in Table 1; that is, carburized steel materials, were carburized for ten hours at 900° C. to 960° C. The thus-carburized steel materials were hardened for one hour at 800° C. to 860° C. The steel materials were then tempered at 160° C. to 200° C. As shown in FIG. 5B, steel materials according to Examples 1, 4, and 6 and that according to Comparative Example 2; that is, through-hardened steel materials, were hardened for one hour at 800° C. to 860° C. Subsequently, the steel materials were tempered at 160° C. to 200° C.

The thus-manufactured steel materials were subjected to ultrasonic flaw detection according to the method described in Japanese Patent Application Laid-Open No. 337530/1999. For each steel type, the inner rings 1, each having non-metallic intervening material (an imperfection) of the size provided in Table 1 and located in the position provided in the same were selected and subjected to a test. With regard to the size of non-metallic intervening material, a plurality of inner rings 1 (for each type of steel material) were tested beforehand. The intensities of the thus-detected imperfection echoes were ascertained. Further, the length and width of each of the thus-found imperfections were actually ascertained by means of additional grinding of the bearing from the raceway surface 2. The relationship between the intensity of an ultrasonic echo and the size of the imperfection was defined for each of the inner rings 1. Thus, the bearing inner rings 1 provided Table 1 were selected.

Figure 6:
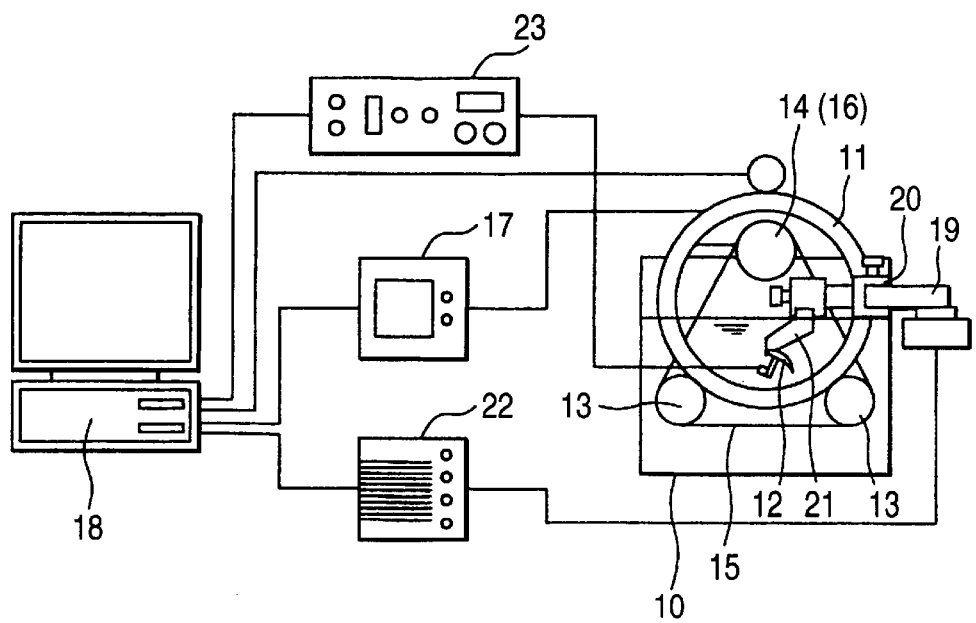
FIG. 6 shows an ultrasonic flaw detector.

FIG. 6 is a schematic diagram showing the ultrasonic flaw detector. Reference numeral 10 designates a tank in which water serving as a ultrasonic wave transmission medium is stored. A raceway ring 11 of a rolling bearing which is an object of inspection and a ultrasonic flaw detection probe 12 are immersed in the water in the tank 10. A probe of point focus type, which has high directivity and has low sensitivity to the influence of curvature of the raceway ring 11, is employed as the ultrasonic flaw detection probe 12. The raceway ring 11 is placed on two pulleys 13 which are immersed in the tank 10 and horizontally spaced apart from each other. A belt 15 is wrapped into a triangular shape

TABLE 1

| No. | Steel Type | Length as defined by the square root of area of maximum imperfection √(length × width) (μm) | Size of non-metallic debris [length × width] (μm) | Depth from raceway surface (mm) | Life until crack formation (×10⁶ rev) |
| --- | --- | --- | --- | --- | --- |
| Example 1 | SUJ2 | 50 | 60 × 42 | 1 | 100 or more |
| Example 2 | SCR420 | 100 | 125 × 80 | 1.5 | 100 or more |
| Example 3 | SCM435 | 180 | 205 × 158 | 3.2 | 100 or more |
| Example 4 | SUJ2 | 200 | 330 × 120 | 4.5 | 88 |
| Example 5 | SAE4320 | 195 | 505 × 75 | 2 | 92 |
| Example 6 | SUJ3 | 150 | 180 × 125 | 0.8 | 95 |
| Comparative Example 1 | SCR420 | 220 | 480 × 100 | 5 | 58 |
| Comparative Example 2 | SUJ2 | 250 | 300 × 208 | 1.2 | 18 |
| Comparative Example 3 | SCM435 | 220 | 510 × 95 | 0.8 | 40 | around the pulleys 13 and a pulley 14 fastened to a motor shaft of a rotary drive motor 16. The rotary drive motor 16 is controlled by means of a controller 18 via a motor drive control amplifier 17. The raceway ring 11 placed on the pulleys 13, 14 is rotated at predetermined speed by means of driving action of the rotary drive motor 16. Here, the controller 18 is constituted of a personal computer or a like device equipped with display means such as a CRT. The ultrasonic flaw detection probe 12 is mounted, via a probe mount 21, on an X-Y stage 20 supported by a linear guide device 19 situated so as to be movable along an axial direction of the raceway ring 11. The probe 12 is disposed so as to oppose the raceway surface 2 of the raceway ring 11. The probe 12 emits, toward the raceway surface of the raceway ring, ultrasonic pulses corresponding to voltage signals output from respective ultrasonic flaw detectors, and receiving echoes reflected from the raceway ring. The thus-received echoes are converted into a voltage signal, and the voltage signal is transmitted to a ultrasonic flaw detector 23. In accordance with an instruction output from the controller 18, the ultrasonic flaw detector 23 transmits to the ultrasonic flaw detection probe 12 an instruction signal consisting of a voltage signal. Further, the detector 23 sends to the controller 18 flaw detection information prepared on the basis of the transmitted and received signals, and the controller 18 displays the information on the CRT. The linear guide 19 moves the ultrasonic flaw detection probe 12 in the axial direction of the raceway ring 11 through an unillustrated servo motor controlled by a linear guide controller 22. When a rotary encoder provided on an outer circumferential surface of the raceway ring 11 detects that the raceway ring 11 has made one rotation (through 360°), the linear guide controller 22 controls the servo motor in accordance with an instruction output from the controller 18, there by moving the ultrasonic flaw detection probe 12 over a predetermined distance in the axial direction of the raceway ring 11. As a result, all cross sections located below the overall raceway surface of the raceway ring 11 are subjected to flaw detection. In the present embodiment, an outer ring is illustrated as the raceway ring 11. However, if the position of the probe 12 and those of the pulleys 13 are switched, the present embodiment is also applicable to an inner ring.

Flaw detection conditions for the ultrasonic flaw detector were set as follows:

Probe: point focus type (a transducer diameter of 6 mm)

Frequency: 15 MHz

In the present example, in relation to the area from the surface to a depth of about 2 mm, an incident angle of ultrasonic waves was set such that ultrasonic waves enter the inside of the inner ring 1 at an angle of 25°. A water distance from a water surface was set to 25 mm. In relation to an area deeper than a depth of 2 mm, the incident angle of the ultrasonic waves that have entered the ring was set to 5°. Further, a water distance was set to 15 mm. A flaw located at an arbitrary depth was detected by use of these settings in combination.

Cylindrical rolling bearings NU3336 having the inner rings 1 satisfying the requirements provided in Table 1 were manufactured through use of the inner rings 1 that had been prepared through the foregoing treatment.

As shown in FIG. 4, a tapered shaft 31 was press-fitted into each of the thus-manufactured cylindrical rolling bearings 30. Fitting stress (200 MPa) was imparted to the inner rings 1. In this state, the tapered shafts 31 were rotated under a radial load of 38000N and at a rotating speed of 1800 rpm. Thus, rolling stress was imparted to the raceway surface 2 of each inner ring 1, and for each inner ring the total number of rotations before axial cracking occurred was examined.

As shown in FIG. 4, reference numeral 32 designates a flow detected by ultrasonic flaw detection.

Figure 7:
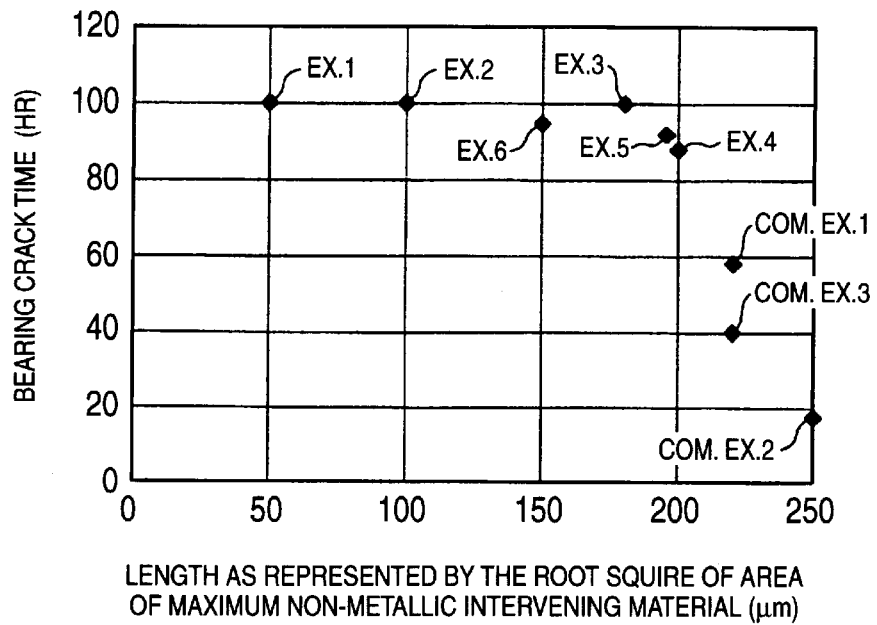
FIG. 7 is a plot showing the relationship between a length as represented by the root square of area of non-metallic intervening material acting as an imperfection and a bearing crack time.

Test results are shown in FIG. 7 and Table 1. As shown in FIG. 7, diamond Example X (X designates 1 through 6) shows results for Example X (X designates 1 through 6) shown in FIG. 1, and diamond Comparative X (X designates 1 through 3) shows results for Comparative Example X (X designates 1 through 3).

As can be seen from the results, all the bearings according to Examples 1 through 6, each including an imperfection (non-metallic intervening material) having a length of 0.2 mm or less as represented by the root square of area of the imperfection, have long crack life. In contrast, the bearings according to Comparative Examples 1 through 3, each including an imperfection having a side of 0.2 mm or more in length, have short crack life.

In connection with a survey on the relationship between the length and width of non-metallic intervening material, as proposed in Japanese Patent Application Laid-Open No. 337530/1999, the flaking life of a bearing can be improved by means of setting the length of an imperfection to 0.5 mm or less. However, in the present invention, limitations on the width of an imperfection as well as those on the length of the same are important for prolonging the flaking life of a bearing. Hence, the size of an imperfection is defined as a length as represented by the root square of area of an imperfection, in consideration of the width and length of the imperfection.

For instance, it is understood from Example 5 that the crack life of a bearing becomes longer if the width of the imperfection is small even when the imperfection has a length in excess of 0.5 mm. In contrast, from Comparative Example 3 in which the imperfection has a large width, a length of 0.5 mm, and a length in excess of 0.2 mm as represented by the root square of area of the imperfection, the crack life of the bearing is short. Further, in the case of Comparative Example 1 in which the imperfection has a length of under 0.5 mm, the crack life of the bearing is short.

As mentioned above, even when the imperfection has a length in excess of 0.5 mm, occurrence of cracking in the bearing can be prevented, by means of limiting the size of an imperfection (including an aggregate of pieces of non-metallic intervening material) contained in a controlled volume of all cross sections of the bearing raceway ring 1 so as not to exceed a maximum length of 0.2 mm as represented by the root square of area of the imperfection.

Example 2

There is now provided an example pertaining to limitation of surface roughness.

Figure 8:
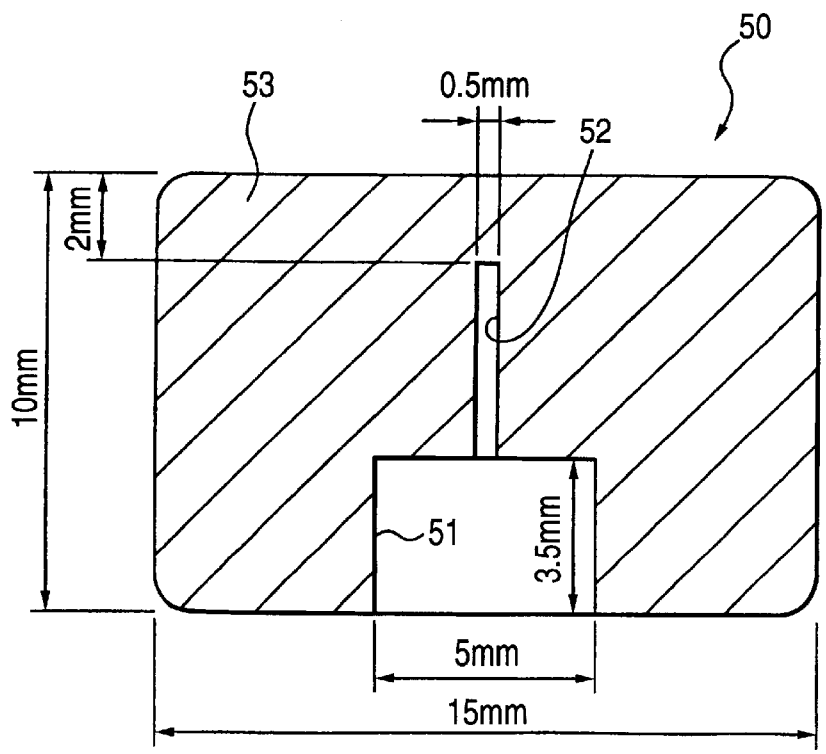
FIG. 8 shows the geometry of a test piece.

Test pieces 50 such as that shown in FIG. 8 were manufactured by means of machining the bearings employed in Example 1, and the test pieces 50 were subjected to a surface roughness test.

Each of the test pieces 50 has a cylindrical shape having a diameter of 15 mm and a height of 10 mm. A cylindrical recess 51 having a diameter of 5 mm and a height of 3.5 mm was formed in the bottom center of each test piece 50. Further, a bore 52 having a diameter of 0.5 mm was vertically formed in the center of the recess 51 to a position located 2 mm below an upper surface 53.

The upper surface 53 was taken as a flaw detection surface, and the roughness of the upper surface 53 was changed in various manners. Thus, a ratio of the intensity of an artificial imperfection echo to noise was determined, thereby examining failure or success in detecting an imperfection.

<Flaw Detection Conditions>

Probe: point focus type (transducer diameter of 6 mm)

Frequency: 15 MHz

The incident angle of the ultrasonic waves that have entered the test piece 50 was set to 5°, and the water distance was set to 15 mm.

Figure 9:
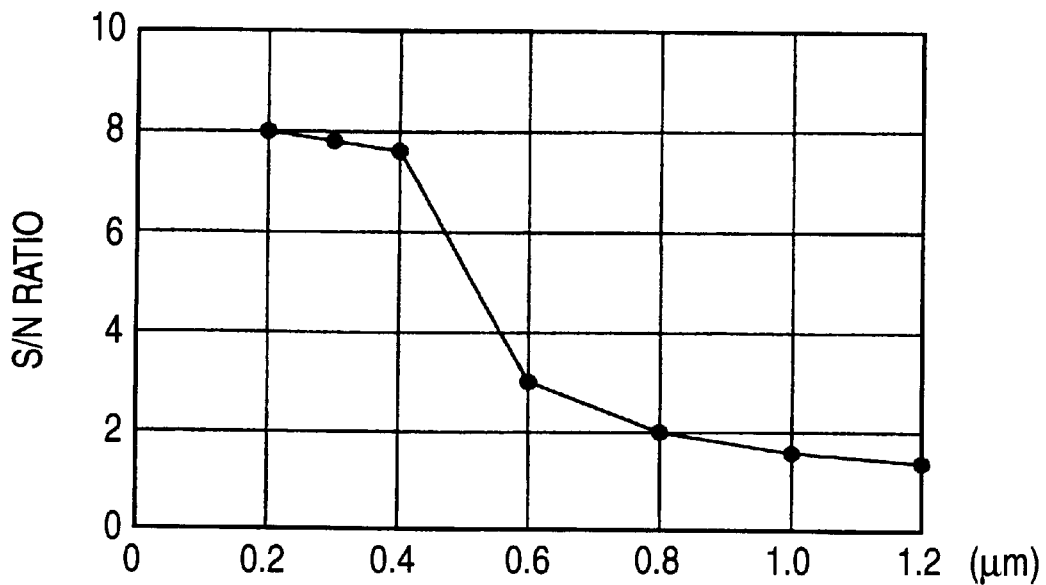
FIG. 9 is a plot showing the relationship between the surface roughness of a raceway surface and a signal-to-noise ratio.

Test results are shown in FIG. 9.

As can be seen from FIG. 9, superior detection intensity (signal-to-noise ratio) is attained before the surface roughness exceeds 0.4 μmRa. However, when the surface roughness exceeds 0.4 μmRa, the detection intensity drops, there by posing difficulty in finding an imperfection smaller than a size of 0.5 mm.

Figure 10:
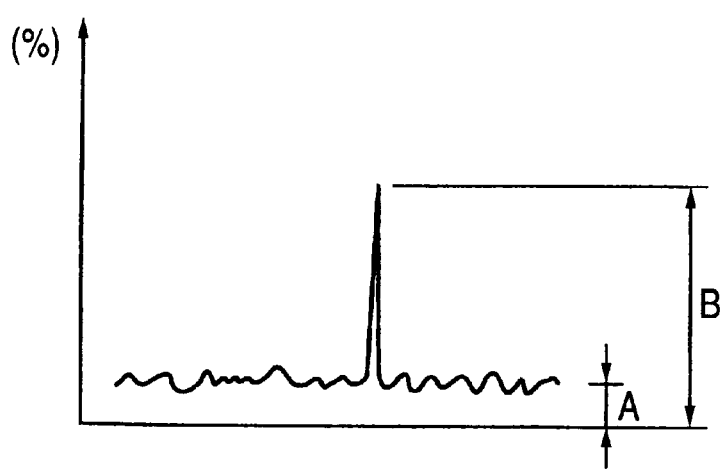
FIG. 10 is a graph for describing a signal-to-noise ratio.

As shown in FIG. 10, the signal-to-noise ratio means a ratio of base noise A (%) acting as background noise to a signal B (imperfection) (%).

As mentioned above, it is understood that small imperfections of tens of micrometers can be detected, by means of limiting the surface roughness of the raceway surface 2 to a value of 0.4 μmRa or less.

Although the above description has been provided from the viewpoint of cylindrical bearings, the present invention can be similarly applied to a tapered rolling bearing or a ball bearing.

Example 3

An example of the present invention will now be described.

Tapered rolling bearings HR32017XJ were manufactured from steel materials provided in Table 2. Outer and inner rings of each of the thus-manufactured tapered rolling bearings were subjected to ultrasonic flaw detection, thereby detecting non-metallic intervening material located immediately below a raceway surface.

Ultrasonic flaw detection was performed under the following flaw detection conditions, through use of the method described in Japanese Patent Application Laid-Open No. 337530/1999. An rectangular-parallelepiped artificial imperfection measuring 0.05 mm deep, 0.05 mm wide, and 5 mm long was formed in the raceway surface of a previously-manufactured bearing. The sensitivity of the ultrasonic flaw detector was calibrated through use of this artificial imperfection, and flaws in the raceway surface of the bearing were detected.

Bearings for which pieces of intervening material having the sizes shown in Table 2 were detected from the respective raceway surfaces were subjected to a bearing life test, whereby the size of non-metallic intervening material and a flaking time (i.e., life) were examined.

With regard to the size of non-metallic intervening material, a plurality of inner and outer rings (for each type of steel material) were tested beforehand. The intensities of the thus-detected imperfection echoes were ascertained. Further, the length and width of each of the thus-found imperfections were actually ascertained by means of additional grinding of the bearing from the raceway surface 2. The relationship between the intensity of an ultrasonic echo and the size of the imperfection was defined for each of the inner rings 1. Thus, the bearing inner rings 1 provided Table 2 were selected.

Test conditions are as follows:

<Ultrasonic Flaw Detection Conditions and Method>

Inspection was performed through use of an ultrasonic flaw detector such as that shown in FIG. 6. Flaw detection was performed by the immersion method. Flaw detection conditions are provided below.

Probe: point focus type (transducer diameter of 6 mm)

Frequency: 10 MHz

In the present example, the entire raceway surface was subjected to flaw detection such that flaws were detected from the surface to a depth of about 2 mm. The probe was set such that the incident angle of the ultrasonic waves that have entered the ring assumes 18°. Further, the water distance was set to 20 mm. Here, an incident angle of 18° means that ultrasonic waves enter the raceway surface serving as an inspection surface at an angle of 18° with reference to the vertical direction.

TABLE 2

| No. | Steel Type | Part to be evaluated | Width (mm) | Length (mm) | √area (mm) | Flaking Life (hr) | |
|---|---|---|---|---|---|---|---|
| Example 1 | SAE4320 | Outer Ring | 0.05 | 0.8 | 0.20 | 700 or more | — |
| Example 2 | | | 0.04 | 1 | 0.20 | 700 or more | — |
| Example 3 | | | 0.07 | 0.45 | 0.18 | 700 or more | — |
| Example 4 | | | 0.1 | 0.3 | 0.17 | 700 or more | 840 |
| Example 5 | | | 0.17 | 0.2 | 0.18 | 700 or more | 790 |
| Example 6 | | | 0.04 | 0.5 | 0.14 | 700 or more | — |
| Example 7 | | | 0.05 | 0.2 | 0.10 | 700 or more | 900 or more |
| Example 8 | | | 0.04 | 0.6 | 0.15 | 700 or more | 900 or more |
| Comparative Example 1 | SAE4320 | Outer Ring | 0.1 | 0.5 | 0.22 | 630 | X |
| Comparative Example 2 | | | 0.12 | 0.8 | 0.31 | 453 | X |
| Comparative Example 3 | | | 0.3 | 0.4 | 0.35 | 480 | X |
| Comparative Example 4 | | | 0.3 | 0.3 | 0.30 | 505 | X |
| Comparative Example 5 | | | 0.1 | 1 | 0.32 | 608 | X |
| Example 9 | SUJ2 | Outer Ring | 0.06 | 0.7 | 0.20 | 700 or more | — |
| Example 10 | SCM435 | Outer Ring | 0.1 | 0.4 | 0.20 | 700 or more | — |
| Example 11 | SAE4320 | Inner Ring | 0.05 | 0.8 | 0.20 | 700 or more | — |

When a flaw was detected through flaw detection, the size of non-metallic intervening material was determined, by means of computation of a ratio of the intensity of the imperfection to the intensity of the artificial imperfection (i.e., the ratio of area) and by reference to the relationship between the intensity of actual intervening material and the thus-computed intensity ratio. Thus, the imperfection was ascertained to be the intervening material of maximum size (hereinafter called "maximum intervening material") located in the raceway surface of the bearing. The bearings provided in Table 2 were subjected to a test.

For bearings from which the maximum intervening material has been found, a determination was made as to whether or not intervening material having a size √(area) of 0.1 mm or more is located in the other area of the bearing; that is, as to whether or not pieces of intervening material located in the other location assume a size √(area) of 0.1 mm or less. More specifically, the bearings were ascertained to have no intervening material which would exert an influence, except for the maximum intervening material provided in Table 2, in the other location.

Verification that the estimated sizes of the pieces of intervening material match sizes of actual pieces of intervening material was performed, by means of grinding the detected imperfection until the top of the imperfection becomes parallel with the raceway surface, finding non-metallic intervening material, and examining the maximum diameter of the intervening material through microscopic observation. Thus has been ascertained that no substantial difference exists between the estimated sizes and the actual sizes.

<Bearing Life Test>

Figure 11:
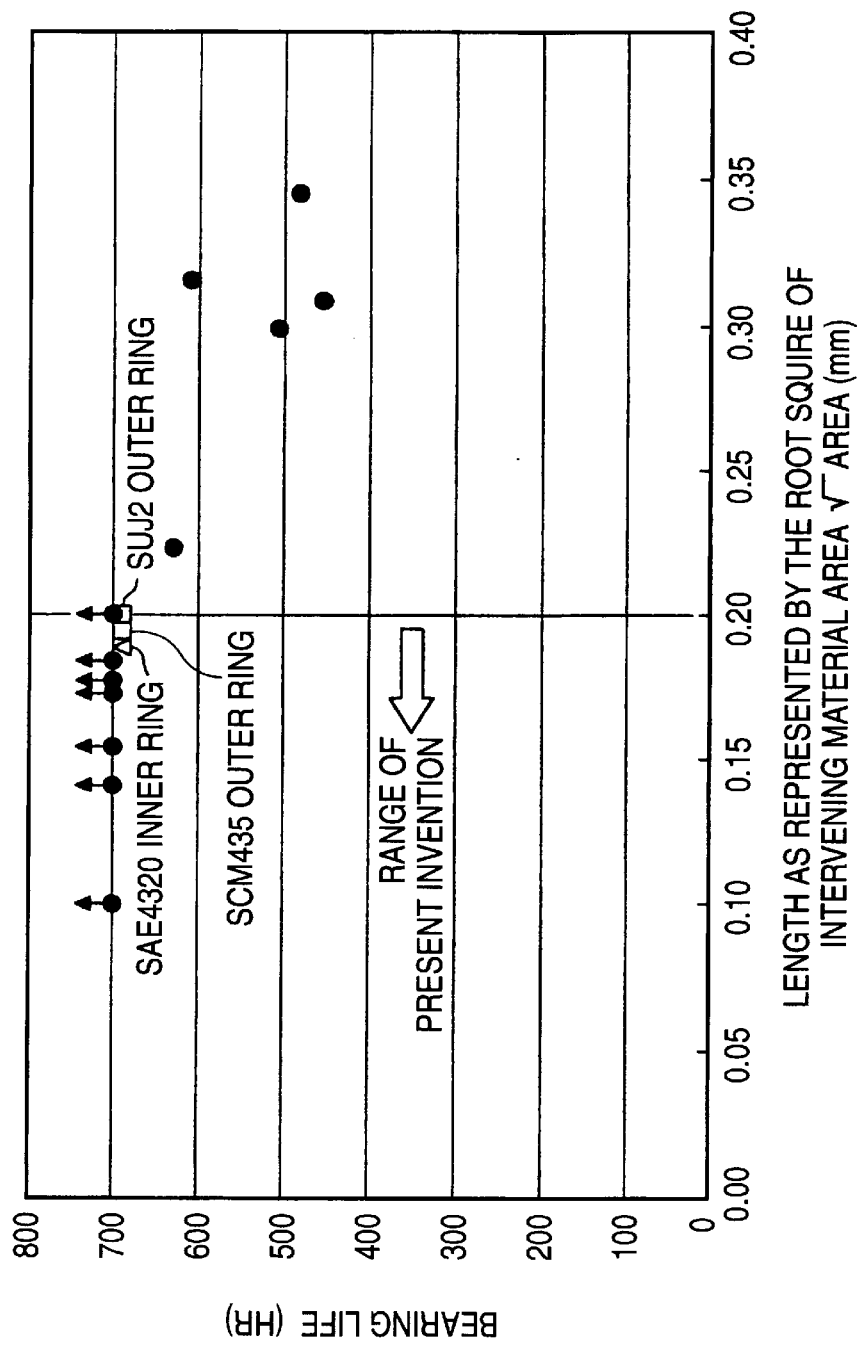
FIG. 11 is a plot showing the relationship between a length as represented by the root square of area of intervening material and the life of a bearing according Example 3.
Figure 12:
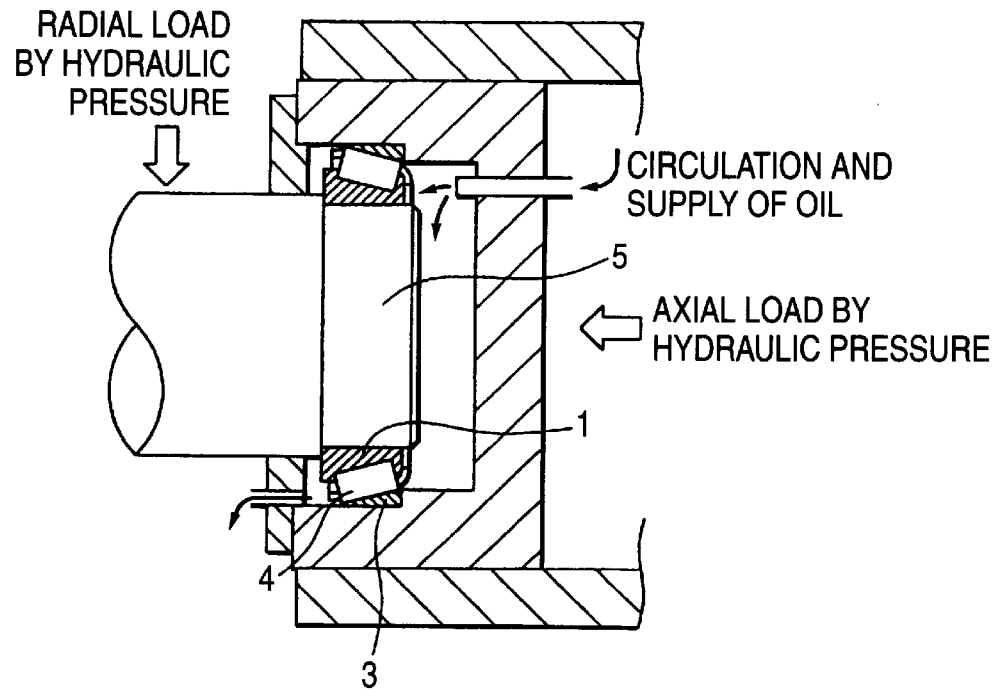
FIG. 12 shows a tester employed in Example 3.

Inner and outer rings for bearings were manufactured from the steel materials shown in FIG. 2, and the thus-manufactured bearings were subjected to life test by use of a tester shown in FIG. 12. FIG. 11 is a plot providing a summary of test results. In FIG. 12, reference numeral 1 designates an inner ring; 3 designates an outer ring; 4 designates a rolling element; and 5 designates a rotator.

Test conditions are as follows:
Bearing: HR32017XJ
Rotational speed: 2000 min$^{-1}$
Lubricant: VG68
Radial load: 43000N
Axial load: 8600N
Contact pressure: P/C=0.3
Computation of life: 457 hr.

In relation to the bearing used for rotating an inner ring, the outer ring 3 becomes a stationary ring. The area of the raceway surface of the outer ring 3, which becomes a load zone, is exposed to the harshest fatigue condition. For this reason, the outer ring 3 is selected as a component to be evaluated in Table 2. The employed inner ring 1 is formed from the same material as that of the outer ring 3 and finished to the same hardness as that of the outer ring 3. HRC62 to 64 manufactured by hardening and tempering SUJ-2 was used for the rolling elements 4.

The test was terminated after 700 hrs., which represents 1.5 times the computed life of the bearings. As a result of the test, the bearings having imperfections in excess of a size √(area) of 0.2 mm were susceptible to flaking. In contrast, the bearings having imperfections of a size √(area) of less than 0.2 mm were not susceptible to flaking even after having been tested in excess of 700 hrs. Further, the bearings according to Examples 7 and 8 which have imperfections of a size √(area) of 0.15 mm or less as shown in Table 2 were not susceptible to flaking even when the bearings had been tested for more than 900 hrs.; that is, twice the computed life of the bearings, in the life test in excess of 700 hrs. When the bearings according to Examples 3, 4 were continuously subjected to the test, the bearings were susceptible to flaking after having been tested for a period of time equal to about a twice the computed life of the bearings.

In order to realize a long-life bearing, the size √(area) is desirably set to a value of 0.2 mm or less; more preferably, a value of 0.15 mm or less.

In relation to heat treatment of the steel materials, the carburized steel materials were subjected to heat treatment through a carburization process, a hardening process, and a tempering process as shown in FIGS. 5A and 5B. The through-hardened steel was produced by means of heat treatment; that is, hardening and tempering, and then polishing.

The steel materials matching adapting to the present invention can be adapted to all types of steel products; that is, carburized steel and through-hardened steel which have hitherto been field-proven as common bearing steel. SUJ2 and SCM435 are used for Examples 9, 10. The bearings have a size √(area) of 0.2 mm or less and are of long life.

The steel materials are similarly applied to inner and outer rings as well as to rolling elements. For Example 11, the bearing that has been subjected to ultrasonic inspection in the same manner as the outer ring was subjected to the test. Since the bearing has a size √(area) of 0.2 mm or less, the bearing is of long life. For the sake of ascertainment, the inner ring was evaluated in connection with Example 11 (the same applies to the outer ring), and no flaking arose in the bearing even when 700 hrs had elapsed.

Example 4

An example of the present invention will now be described.

Cylindrical rolling bearings NU3236 were manufactured from steel materials provided in Tables 3 through 5. Outer and inner rings 3, 1 of each of the thus-manufactured rolling bearings were subjected to ultrasonic flaw detection, thereby detecting non-metallic intervening material located immediately below a raceway surface. Tables show only data for the outer rings 3.

TABLE 3

F = 270000 N, $(\tau_{st})_{MAX}$ = 422 MPa, √(area)$_{MAX}$ = 0.22 (HV = 740)

| No. | Steel Type | Part to be evaluated | Width (mm) | Length (mm) | √area (mm) | Flaking Life (hr) | |
|---|---|---|---|---|---|---|---|
| Comparative Example 1 | SAE4320 | Outer Ring | 0.04 | 1.1 | 0.21 | 840 | X |
| Comparative Example 2 | | | 0.2 | 0.5 | 0.32 | 1205 | X |
| Example 1 | | | 0.05 | 0.7 | 0.19 | 1500 or more | ○ |

TABLE 4

F = 312000 N, $(\tau_{st})_{MAX}$ = 450 MPa, $\sqrt{(area)}_{MAX}$ = 0.15 (HV = 740)

| No. | Steel Type | Part to be evaluated | Width (mm) | Length (mm) | $\sqrt{area}$ (mm) | Flaking Life (hr) | |
|---|---|---|---|---|---|---|---|
| Comparative Example 3 | SAE4320 | Outer Ring | 0.18 | 0.2 | 0.19 | 1045 | X |
| Comparative Example 4 | | | 0.1 | 0.3 | 0.17 | 920 | X |
| Example 2 | | | 0.15 | 0.1 | 0.12 | 1500 or more | ○ |
| Example 3 | | | 0.04 | 0.5 | 0.14 | 1500 or more | ○ |

TABLE 5

F = 340000 N, $(\tau_{st})_{MAX}$ = 470 MPa, $\sqrt{(area)}_{MAX}$ = 0.11 (HV = 740)

| No. | Steel Type | Part to be evaluated | Width (mm) | Length (mm) | $\sqrt{area}$ (mm) | Flaking Life (hr) | |
|---|---|---|---|---|---|---|---|
| Comparative Example 5 | SAE4320 | Outer Ring | 0.05 | 0.5 | 0.16 | 789 | X |
| Comparative Example 6 | | | 0.1 | 0.17 | 0.13 | 711 | X |
| Example 4 | | | 0.05 | 0.2 | 0.10 | 1500 or more | ○ |

The ultrasonic flaw detection method was carried out under the following flaw detection conditions. As in the case of Example 3, a rectangular-parallelepiped artificial imperfection measuring 0.05 mm deep, 0.05 mm wide, and 5 mm long was formed in the raceway surface of a previously-manufactured bearing. The sensitivity of the ultrasonic flaw detector was calibrated through use of this artificial imperfection, and flaws in the raceway surface of the bearing were detected.

Bearings for which pieces of intervening material having the sizes shown in Tables 3 through 5 were detected from the respective raceway surfaces were subjected to a bearing life test, whereby the size of non-metallic intervening material and a flaking time (i.e., life) were examined according to the test conditions.

With regard to the size of non-metallic intervening material, a plurality of inner and outer rings (for each type of steel material) were tested beforehand. The intensities of the thus-detected imperfection echoes were ascertained. Further, the length and width of each of the thus-found imperfections were actually ascertained by means of additional grinding of the bearing from the raceway surface 2. The relationship between the intensity of an ultrasonic echo and the size of the imperfection was defined for each of the inner rings 1. Thus, the bearing outer rings provided Tables 3 through 5 were selected.

Test conditions are as follows:
<Ultrasonic Flaw Detection Conditions and Method>

Inspection was performed through use of an ultrasonic flaw detector such as that shown in FIG. 6. Flaw detection was performed by the immersion method. Flaw detection conditions are provided below.

Probe: point focus type (transducer diameter of 6 mm)
Frequency: 10 MHz

In the present example, the entire raceway surface was subjected to flaw detection such that flaws were detected from the surface to a depth of about 2 mm. The probe was set such that the incident angle of the ultrasonic waves that have entered the ring assumes 18°. Further, the water distance was set to 20 mm.

When a flaw was detected through flaw detection, the size of non-metallic intervening material was determined, by means of computation of a ratio of the intensity of the imperfection to the intensity of the artificial imperfection (i.e., the ratio of area) and by reference to the relationship between the intensity of actual intervening material and the thus-computed intensity ratio. Thus, the imperfection was ascertained to be the maximum intervening material located in the raceway surface of the bearing. The bearings provided in Tables 3 through 5 were subjected to a test. For bearings from which the maximum intervening material has been found, a determination was made as to whether or not intervening material having a size $\sqrt{(area)}$ of 0.1 mm or more is located in the other area of the bearing. More specifically, the bearings were ascertained to have no intervening material which would exert an influence, except for the pieces of maximum intervening material provided in Tables 3 through 5, in the other location.

As in the case of Example 3, the outer ring is taken as an object of evaluation, and the same conditions as employed in the examples were set for the inner ring and the rolling elements.

<Bearing Life Test>
Bearing: NU3236
Rotational speed: 1500 min$^{-1}$
Lubricant: grease
Radial load: 270000N, 312000N, 340000N
Computation of life: 186 to 400 hrs.

Figure 13:
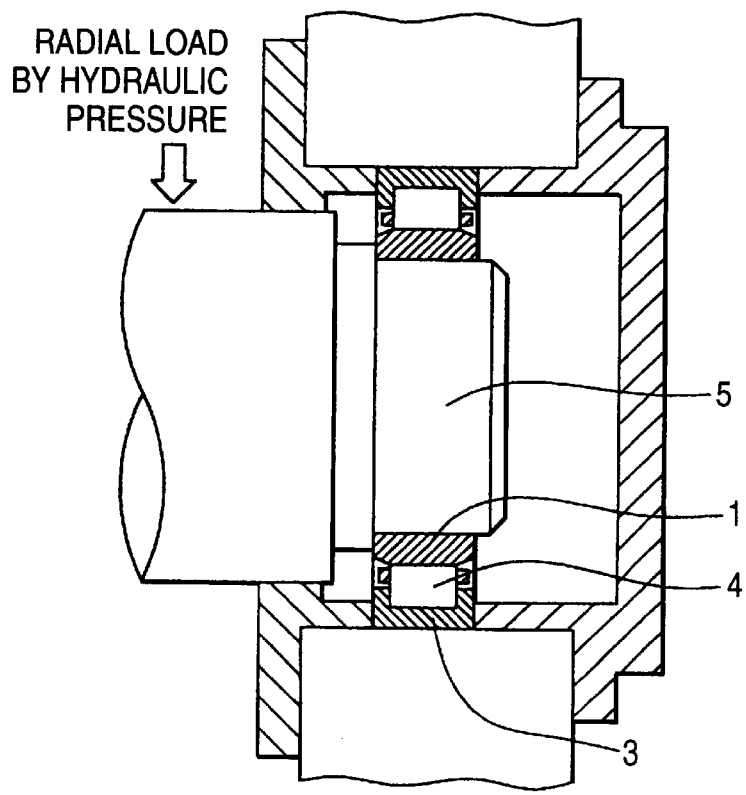
FIG. 13 shows a tester employed in Example 4.

The data for the inner and outer rings of the bearings are shown in Tables 3 through 5. The outer rings were subjected to life test through use of the tester shown in FIG. 13. The test was terminated after 1500 hrs., which represents four times the computed life of the bearings (i.e., the life of the most long-lived bearing). As a result of the test, as shown in Tables 3 through 5, flaking arose in the bearings having pieces of intervening material in excess of the critical value obtained by substituting the maximum shearing force $\tau_{st}$ determined from the test conditions into the following equation; that is, $\sqrt{(area)}_{MAX} = [(1.56 \cdot Hv + 187) \times (0.77/(\tau_{st})_{MAX})]^6$. No flaking arose in the other bearings.

The bearing shown in Table 3 has a critical value critical value $\sqrt{(area)}_{MAX}$ of 0.22; the bearing shown in Table 4 has a critical value critical value $\sqrt{(area)}_{MAX}$ of 0.15; and the bearing shown in Table 5 has a critical value critical value $\sqrt{(area)}_{MAX}$ of 0.11.

Although the Examples employ the ultrasonic flaw detection probe of point focus type as an example, a probe of flat beam type may be employed. In accordance with the form of an imperfection to be detected, a probe is preferably determined.

Example 5

Outer rings for tapered rolling bearings HR32017XJ were manufactured. The raceway surfaces of the outer rings were subjected to flaw detection through use of the ultrasonic flaw detection method described in connection with Example 3.

Flaw detection conditions which are the same as those employed in Example 3 were employed.

More specifically, a bearing raceway ring to be inspected and the probe for flaw detection were immersed in water. Flaws in the raceway surfaces were detected by means of the surface wave flaw detection method and the angle beam method. Bearings for which a signal-to-noise ratio of 3 or more was obtained by means of either the surface wave flaw detection method or the angle beam method were recognized as defectives. Intensities of imperfection echos were recorded according to the respective methods. Twenty or more bearings were evaluated as defectives, because they have a noise level of 5 to 7 under the following conditions.

Five hundreds or more bearings were subjected to inspection. From among defectives and non-defectives, the bearings provided in Examples 1 through 14 were selected.

Table 6 shows the heights of echoes originating from imperfections in the respective bearings. In order to ascertain the geometry and form of the thus-detected imperfections, the specified positions of imperfections were gradually ground from the raceway surface in the circumferential direction of the bearing. The width and length of each of the imperfections (i.e., pieces of intervening material) were examined. Results of examination are also provided in Table 6.

type as described in Japanese Patent Application Laid-Open No. 337530/1999 was employed as a method of evaluating the intervening material located immediately below a raceway surface of a bearing. It can be seen that pieces of intervening material having a width of 0.1 mm or more could be detected with superior signal-to-noise ratios. Further, it is seen that the surface wave flaw detection method using the probe of flat beam type according to the present invention exhibited the sufficient detection capability.

As can be seen from Examples 7 through 11, according to the conventional method (using the probe of point focus type), the capability of detecting pieces of intervening material having a width of 0.1 mm or less and a length of 1 mm or more is low, and the bearings including such intervening material were taken as non-defective in some cases.

In contrast, it is understood that, under the method according to the present invention (i.e., the surface wave flaw detection method using the probe of flat beam type), sufficient detection capability is exhibited, thereby enabling detection of the bearings including the above-described intervening material as defectives.

As can be seen from Examples 12, 13, the bearings including pieces of intervening material having a length of 0.25 mm or less were taken as defectives under the conventional method (using the probe of point focus type). In contrast, under the method according to the present invention (i.e., the surface wave flaw detection method using the probe of flat beam type), some Examples show that the bearings including the pieces of intervening material having a length of 0.25 mm or less are not taken as defectives.

As is evident from Example 14, some bearings are determined to be non-defective by both the conventional method (using the probe of point focus type) and by the method according to the present invention (i.e., the surface wave flaw detection method using the probe of flat beam type).

Consequently, it is understood that implementation of the method according to the present invention (i.e., the surface wave flaw detection method using the probe of flat beam type) along with the conventional method enables effective detection of large intervening material having a narrow width but a long length.

TABLE 6

| | Heights of echos from imperfections detected by surface wave method (using probe of flat beam type) | Incident Angle (°) | | Heights of echos from imperfections detected by angle beam method (using probe of point focus type) | Incident Angle (°) | | Imperfection Size Width (mm) | Length (mm) |
|---|---|---|---|---|---|---|---|---|
| Example 1 | 95 | 28–30 | NG | 100 | 19 | NG | 0.50 | 0.80 |
| Example 2 | 80 | | NG | 98 | | NG | 0.30 | 0.40 |
| Example 3 | 50 | | NG | 80 | | NG | 0.25 | 0.30 |
| Example 4 | 40 | | NG | 45 | | NG | 0.18 | 0.25 |
| Example 5 | 30 | | NG | 40 | 25 | NG | 0.12 | 0.22 |
| Example 6 | 40 | | NG | 50 | 14 | NG | 0.20 | 0.30 |
| Example 7 | 85 | 28–30 | NG | 8 | 19 | OK | 0.08 | 3.00 |
| Example 8 | 35 | | NG | 8 | | OK | 0.04 | 1.00 |
| Example 9 | 70 | | NG | 15 | | OK | 0.10 | 3.30 |
| Example 10 | 45 | | NG | 10 | 25 | OK | 0.07 | 1.00 |
| Example 11 | 90 | | NG | 8 | 14 | OK | 0.05 | 5.00 |
| Example 12 | 16 | 28–30 | OK | 45 | 19 | NG | 0.22 | 0.25 |
| Example 13 | 13 | | OK | 35 | | NG | 0.16 | 0.18 |
| Example 14 | 8 | 28–30 | OK | 8 | 19 | OK | 0.05 | 0.10 |

As can be seen from Examples 1 through 6, the conventional angle beam method using the probe of point focus It is seen that combination of these methods preferably enables detection of intervening material of any form.

Example 6

The bearings that have been determined to be defective and non-defective by means of the methods were subjected to a test as to the influence of intervening material on the life of a bearing. Table 7 shows test results.

TABLE 7

| | Heights of echos from imperfections detected by surface wave method (using probe of flat beam type) | Incident Angle (°) | | Heights of echos from Imperfections detected by angle beam method (using probe of point focus type) | Incident Angle (°) | | Ratio of life of object to life L10 | Remarks |
|---|---|---|---|---|---|---|---|---|
| Example 15 | 75 | 28–30 | NG | 95 | 19 | NG | 0.08 | Corresponding to Example 2 |
| Example 16 | 40 | | NG | 8 | | OK | 0.10 | Corresponding to Example 8 |
| Example 17 | 8 | | OK | 8 | | OK | 1.40 | Corresponding to Example 14 |

Example 15 is presumed to have intervening material corresponding to that found in connection with Example 2 in Table 6, on the basis of the height of an echo from an imperfection. The bearing according to Example 15 was determined to be defective according to both flaw detection methods.

Example 16 is presumed to have intervening material corresponding to that found in connection with Example 8 in Table 6, on the basis of the height of an echo from an imperfection. The bearing according to Example 16 was determined to be non-defective according the conventional angle beam method using the probe of point focus type but determined to be defective under the flaw detection method according to the present invention.

Example 17 is presumed to have intervening material corresponding to that found in connection with Example 14 in Table 6, on the basis of the height of an echo from an imperfection. The bearing according to Example 17 was determined to be non-defective according to both flaw detection methods. The height of the echo from the imperfection slightly exceeds noise.

Figure 14:
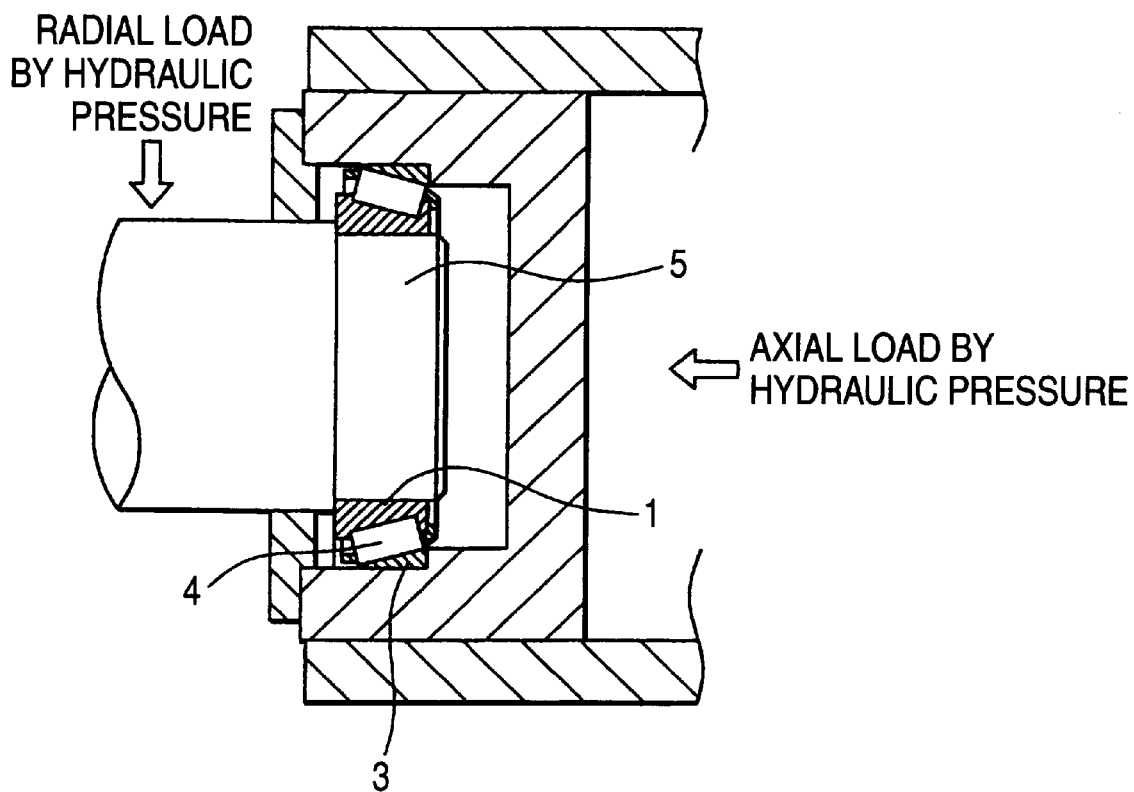
FIG. 14 shows a tester employed in Example 6.

The outer rings 3 of the bearings described in connection with the above three examples were set to the lift tester shown in FIG. 14 such that the positions of the flaws are located in the load range. Then, the outer rings were tested.

The bearings in which no flaw was found were selected beforehand. Then, 20 bearings were subjected to a life test, whereby there was obtained life L10. Provided that life L10 is one, the ratio of life of each of the bearings to life L10 was determined.

Test conditions are as follows:
<Lift Test Conditions>

Bearing: HR32017XJ
Radial load: 35750N
Axial load: 15690N
Rotational speed: 1500 min$^{-1}$
Lubricant: grease Table 2 also provides results of this life test.

The bearing according to Example 15 that have been determined to be defective according to the conventional method (using the probe of point focus type) and by the method according to the present invention (i.e., the surface wave flaw detection method using the probe of flat beam type) was short-lived, and flaking arose in the position of the imperfection.

The bearing according to Example 16 that have been determined to be non-defective according the conventional angle beam method (using the probe of point focus type) but determined to be defective according to the present invention (i.e., the surface wave flaw detection method using the probe of flat beam type) was short-lived, and flaking arose in the position of the imperfection.

The bearing according to Example 17 that have been determined to be non-defective according to the conventional method (using the probe of point focus type) and by the method according to the present invention (i.e., the surface wave flaw detection method using the probe of flat beam type) was lived longer than life L10. It is understood that the bearing that has been determined to be non-defective by the method according to the present invention is not harmful to the life of the bearing.

Form the above, the bearing including the imperfection detected by the flaw detection method according to the present invention is understood to be short-lived, and use of only the conventional method is also understood to be insufficient.

Even intervening material having a width of 0.1 mm or less is harmful to the life of a bearing if the intervening material has a length of 1 mm or more. A combination of the conventional method using the probe of point focus type and the surface wave flaw detection method using the probe of flat beam type according to the present invention is optimal for detecting an imperfection deleterious to the life of a bearing.

As has been described, the rolling bearing according to the first aspect of the present invention yields the advantage of obviating a concern about occurrence of cracking even in a harsh environment as in the case of a commercial and of preventing a bearing from becoming short-lived in terms of rolling fatigue life.

The inventions defined in the second and third aspects of the present invention yield an advantage of the ability to provide a bearing which is assured of assured of involving no concern about occurrence of a short-lived or cracked bearing, even when used under a condition in which the bearing is subjected to high-cycle rolling fatigue due to high-speed rotation, as in the case of a bearing for use in a railcar such as the Shinkansen or a bearing for use in steel working facilities. Particularly, the invention defined in third aspect of the present invention is effective for a bearing to be used in harsh working conditions.

According to the ultrasonic flaw detection method according to the fourth aspect of the present invention, imperfections which are present in a bearing and are deleterious to the life of the bearing can be detected efficiently. More specifically, there are various types of deleterious imperfections ranging from narrow elongated imperfections to round imperfections. Under the method according to the present invention, all imperfections of different forms can also be detected efficiently.

According to the ultrasonic flaw detection method according to the fifth aspect of the present invention, there is obviated a concern about occurrence of a short-life product, by means of assuring absence of imperfections in an area ranging from a surface or a neighborhood thereof to an inside of a bearing, which area is to be exposed to rolling fatigue stress. Thus, there can be provided a bearing assured of a long life.

While there has been described in connection with the preferred embodiment of the invention, it will be obvious to those skilled in the art that various changes and modifications may be made therein without departing from the invention, and it is aimed, therefore, to cover in the appended claim all such changes and modifications as fall within the true spirit and scope of the invention.

What is claimed is:

1. A rolling bearing that is subject to at least one of repeated stress, fitting stress and hoop stress in its operation comprising:

a bearing raceway ring having a surface which has a roughness of 0.4 μmRa or less and is to serve as a surface to be subject to ultrasonic inspection, and wherein all of imperfections, existing in a volume defined by the sum of all of cross sections each includes an axis of rotation of the raceway ring and extends in parallel to the rotation axis of the raceway ring, have a length of 0.2 mm or less as represented by the square root of area of the imperfection.

2. A rolling bearing comprising:

a bearing raceway ring having a raceway surface which has a roughness of 0.4 μmRa or less and is to serve as a surface to be subject to ultrasonic inspection, and wherein all of imperfections, existing in a volume which is a product of the area of the raceway surface to be ultrasonically inspected and 2% Da depth from the raceway surface to be ultrasonically inspected where Da indicates a diameter of the bearing raceway ring, have a length of 0.2 mm or less as represented by the square root of area of the imperfection.

3. A rolling bearing comprising:

a bearing raceway ring having a raceway surface which has a roughness of 0.4 μmRa or less and is to serve as a surface to be subject to ultrasonic inspection, and wherein all of imperfections, existing in a volume which is a product of the area of the raceway surface to be ultrasonically inspected and 2% Da depth from the raceway surface to be ultrasonically inspected where Da indicates a diameter of the bearing raceway ring, have a length of 0.2 mm or less as represented by the square root of area of the imperfection, or have a length that is represented by the square root of area of the imperfection and also is smaller than $\sqrt{(area)}_{MAX}$ as represented by Eq. (1)

$$\sqrt{(area)}_{MAX} = [(1.56 \cdot Hv + 187) \times (0.77/(\tau_{st})_{MAX})]^6 \qquad (1)$$

where $(\tau_{st})_{MAX}$ indicates the maximum shearing stress (MPa) induced by rolling load on the raceway surface, and Hv identifies Vickers hardness in the position of the maximum shearing stress beneath the raceway surface.

4. The rolling bearing according to claim 1, wherein the imperfections have a length of 0.15 mm or less as represented by the square root of area of the imperfection.

5. The rolling bearing according to claim 2, wherein the imperfections have a length of 0.15 mm or less as represented by the square root of area of the imperfection.

6. The rolling bearing according to claim 3, wherein the imperfections have a length of 0.15 mm or less as represented by the square root of area of the imperfection.

7. The rolling bearing according to claim 3, wherein the imperfections are detected according to a bearing raceway ring ultrasonic imperfection detection method comprising:

transmitting an ultrasonic wave from a ultrasonic detection probe to a surface of a bearing raceway ring to be ultrasonically inspected; and detecting an imperfection of the bearing raceway ring on a basis of an ultrasonic wave echo reflected from the surface of the bearing raceway ring, and wherein the imperfection is detected up to a depth beneath the surface of the bearing raceway ring, by means of at least one of the angle beam imperfection detection method and surface beam imperfection detection method.

8. The bearing raceway ring ultrasonic imperfection detection method according to claim 7, wherein a flat beam probe of non-focus type is used for at least one of the methods.

9. The bearing raceway ring ultrasonic imperfection detection method according to claim 7, wherein the imperfection is detected up to a depth of 2 mm beneath at least a position of the maximum shearing stress beneath the surface of the bearing raceway ring.

10. The bearing raceway ring ultrasonic imperfection detection method according to claim 7, wherein the ultrasonic wave thus transmitted has a frequency in the range from 2 Hz to 15 Hz.

11. The bearing raceway ring ultrasonic imperfection detection method according to claim 7, wherein the detecting steps comprises:

detecting a bearing raceway ring as a non-defecting one if all of imperfection of the raceway surface has a length of 0.2 mm or less as represented by the square root of area of the imperfection.

12. The method according to claim 7, wherein the detecting steps comprises:

detecting a bearing raceway ring as a non-defecting one if all of imperfection of the raceway surface has a length of 0.15 mm or less as represented by the square root of area of the imperfection.

* * * * *